(12) United States Patent
Picken

(10) Patent No.: US 8,428,964 B2
(45) Date of Patent: Apr. 23, 2013

(54) SYSTEM AND METHOD FOR MATCHING HEALTHCARE PROVIDERS WITH CONSUMERS

(75) Inventor: Andrew J. Picken, Pendleton, OR (US)

(73) Assignee: Healthocity, Inc. A Delaware Corporation, Boise, ID (US)

( * ) Notice: Subject to any disclaimer, the term of this patent is extended or adjusted under 35 U.S.C. 154(b) by 215 days.

(21) Appl. No.: 12/777,302

(22) Filed: May 11, 2010

(65) Prior Publication Data

US 2010/0286998 A1  Nov. 11, 2010

Related U.S. Application Data

(60) Provisional application No. 61/177,020, filed on May 11, 2009, provisional application No. 61/313,221, filed on Mar. 12, 2010.

(51) Int. Cl.
*G06Q 10/00* (2012.01)
*G06Q 50/00* (2012.01)

(52) U.S. Cl.
USPC .................. 705/2; 705/3; 705/26.1; 705/26.3

(58) Field of Classification Search .................. 705/2–3, 705/26.1, 26.3
See application file for complete search history.

(56) References Cited

U.S. PATENT DOCUMENTS

| | | | |
|---|---|---|---|
| 5,301,105 A | 4/1994 | Cummings, Jr. | |
| 6,658,431 B1 | 12/2003 | Norman, Jr. | |
| 6,735,569 B1 | 5/2004 | Wizig | |
| 7,383,197 B1 | 6/2008 | Neuman | |
| 7,590,550 B2 | 9/2009 | Schoenberg | |
| 7,653,558 B2 | 1/2010 | Schoenberg | |
| 7,657,479 B2 | 2/2010 | Henley | |
| 7,752,060 B2 | 7/2010 | Hicks et al. | |
| 7,756,721 B1 | 7/2010 | Falchuk et al. | |
| 7,765,146 B2 | 7/2010 | Sakaue et al. | |
| 7,818,183 B2 | 10/2010 | Schoenberg | |
| 7,835,928 B2 | 11/2010 | Schoenberg | |
| 7,848,937 B2 | 12/2010 | Schoenberg | |
| 7,865,377 B2 | 1/2011 | Schoenberg | |
| 7,895,061 B2 | 2/2011 | Schoenberg | |
| 2002/0007290 A1 | 1/2002 | Gottlieb | |
| 2002/0038233 A1 | 3/2002 | Shubov et al. | |
| 2002/0069085 A1 | 6/2002 | Engel et al. | |
| 2002/0087533 A1 | 7/2002 | Norman, Jr. | |
| 2003/0046113 A1 | 3/2003 | Johnson et al. | |
| 2003/0120513 A1 | 6/2003 | Samaquial | |
| 2003/0187691 A1 | 10/2003 | Dutt et al. | |

(Continued)

FOREIGN PATENT DOCUMENTS

| | | |
|---|---|---|
| JP | 2006-048423 A | 2/2006 |
| KR | 10-2001-0095363 A | 11/2001 |

OTHER PUBLICATIONS

Lando, Maximizing the Internet to market to consumers, Sep./Oct. 2002, Healthcare Executive, pp. 8-14.*
International Search Report and Written Opinion for Appl. No. PCT/US2010/034300 dated Dec. 28, 2010.

*Primary Examiner* — Luke Gilligan
(74) *Attorney, Agent, or Firm* — Pearne & Gordon LLP

(57) ABSTRACT

A system and method for providing both healthcare service providers and healthcare product providers a forum for marketing their services directly to healthcare consumers with the system facilitating the payments from the consumers to the providers.

23 Claims, 7 Drawing Sheets

U.S. PATENT DOCUMENTS

| | | |
|---|---|---|
| 2003/0195838 A1 | 10/2003 | Henley |
| 2004/0064440 A1 | 4/2004 | Norman, Jr. |
| 2005/0027580 A1 | 2/2005 | Crici et al. |
| 2005/0182660 A1* | 8/2005 | Henley ............... 705/2 |
| 2005/0283383 A1 | 12/2005 | Zammit |
| 2005/0288972 A1 | 12/2005 | Marvin et al. |
| 2006/0015369 A1 | 1/2006 | Bachus et al. |
| 2006/0080146 A1 | 4/2006 | Cook et al. |
| 2006/0122850 A1 | 6/2006 | Ward et al. |
| 2006/0136264 A1 | 6/2006 | Eaton et al. |
| 2006/0190296 A1 | 8/2006 | Hackett et al. |
| 2006/0247968 A1 | 11/2006 | Kadry |
| 2007/0094044 A1 | 4/2007 | Stone et al. |
| 2007/0156455 A1 | 7/2007 | Tarino et al. |
| 2008/0167998 A1 | 7/2008 | Hyte |
| 2009/0094060 A1 | 4/2009 | Johnson et al. |
| 2009/0150296 A1* | 6/2009 | Kirovski et al. ............... 705/80 |
| 2009/0198509 A1 | 8/2009 | Dumoff |
| 2009/0319523 A1 | 12/2009 | Anderson et al. |
| 2010/0017222 A1 | 1/2010 | Yeluri et al. |
| 2010/0070298 A1 | 3/2010 | Kalies |
| 2010/0076788 A1 | 3/2010 | Benja-Athon |
| 2010/0088115 A1 | 4/2010 | Henley |
| 2010/0211411 A1 | 8/2010 | Hudson |
| 2010/0235178 A1 | 9/2010 | Firminger et al. |
| 2010/0268549 A1 | 10/2010 | Hicks et al. |
| 2010/0286998 A1 | 11/2010 | Picken |
| 2011/0022479 A1 | 1/2011 | Henley |

* cited by examiner

SYSTEM AND METHOD FOR MATCHING HEALTHCARE PROVIDERS WITH CONSUMERS

CROSS-REFERENCES TO RELATED APPLICATIONS

This application claims the benefit of provisional application Ser. No. 61/177,020 filed on May 11, 2009, and provisional application Ser. No. 61/313,221 filed on Mar. 12, 2010, both incorporated herein by reference.

FIELD OF THE INVENTION

This application relates generally to a system and method for facilitating the commerce of healthcare products and services. More specifically, this application relates to a system and method for providing both healthcare service providers and healthcare product providers a forum for marketing their services directly to healthcare consumers with the system facilitating the payments from the consumers to the providers.

BACKGROUND OF THE INVENTION

Healthcare service and supply producers have typically tried to achieve success by selling their supplies to consumers in close proximity to their geographic locations. HealthCare Service and Supply (HCS/S) producers generally market their supplies through local media (e.g. newspapers, trade magazines) and direct consumer communication. Local media marketing focused on close proximity geographic areas limits the consumer base of healthcare service and supply providers.

In addition, healthcare service and supply producers offer services in non-specific, general categories. For example, primary care providers typically offer two general services: new patient visits and follow-up patient visits.

HCS/S producers typically do not offer services and supplies specific to known HCS/S consumer needs. For example, HCS/S producers do not offer services to address common HCS/S needs, for example:
  'Diagnosis and treatment of sore throat'; or
  'Evaluation and effective treatment of chronic back pain'; or
  'Evaluation and effective treatment of elderly patient with sudden memory loss'.

General category marketing does not adequately represent the full spectrum of healthcare services and supplies available; whereas offering services and supplies specific to known HCS/S consumer needs would better present useful, high demand HCS/S products and services to the marketplace.

Healthcare service and supply producers typically obtain payment through a combination of third party means and sometimes receive out-of-pocket payments directly from consumers. Thus, there are currently two principal categories of healthcare spending: payment through third party payers (such as insurance companies, for example) and individual payments from consumers. Individual out-of-pocket payment for Healthcare Services and Supplies (HCS/S) is currently a growing trend. Current estimates of annual individual out-of-pocket spending for healthcare services in the United States at the time of this application range from $34 Billion to $850 Billion. Individual out-of-pocket payments constitute a growing proportion of total healthcare spending. However, there is currently no central marketplace available where consumers can search for available healthcare services and supplies based on the specific features of the healthcare service or supply of interest, including: price, availability, quality, producer service quality, physical location, time availability, and based on the current needs of the consumer.

Currently, most consumers tend to pay for health care through third-party payers, such as insurance companies, or the government. However, payments through third party payers are inefficient, cumbersome and administratively complex, and consumers often try to avoid this process. HCS/S producers typically collect payment from third party payers through costly administrative systems. Third party payers attach administrative requirements to payments, which can increase cost and complexity. These requirements reduce Producer quality, efficiency and productivity, and thus the producers would also often like to avoid this process. However, out-of-pocket payments are currently difficult to secure. Thus, HCS/S consumers and producers lack an efficient system to identify, offer, select and transfer payment for healthcare services and supplies.

Furthermore, HCS/S Producers typically maintain excess production capacity that may go to waste. For example, primary care provider office schedules frequently include patient evaluation time slots that are not used, and medical supply companies maintain supply inventories that are not promptly sold.

But currently, there is no organized transaction system for individual out-of-pocket payment for healthcare services and supplies. There is currently no organized transaction system to reduce HCS/S marketplace complexity; to facilitate HCS/S identification, purchase and sales outside of local geographic and media constraints; to facilitate sales of discrete HCS/S to remote locations, to collect HCS/S out-of-pocket payments; to consolidate latent production capacity; and to facilitate Consumer searches for HCS/S based on the specific features of the HCS/S of interest. Although consumers can currently purchase HCS/S with out-of-pocket payments, there is no organized transaction system for facilitating out-of-pocket HCS/S transactions. In addition, although HCS/S consumers can make out-of-pocket payments to HCS/S producers through individual payment plans, these individual payment plans are not coordinated through an organized transaction system. Payment options through these individual payment plans can include payment with credit cards, checks, cash, debit cards and barter transactions. Individual payments are thus typically made in full at point-of-service or in installment plans. These individual payment plans are administratively complex, difficult to enforce, inefficient and expensive.

Needed is a system and method to help overcome one or more of these shortcomings of the current healthcare marketplace.

SUMMARY OF THE INVENTION

Provided is a novel transaction system for healthcare services and supplies. This new system and process applies to the healthcare marketplace by offering a new transaction system for healthcare services and supplies (HCS/S). The main users of this new transaction system will include the consumers and producers of healthcare services and supplies.

One or more of the example systems provide:
1) A connecting system for conducting an organized interactive virtual marketplace for healthcare services and supplies;
2) A transaction system for organizing and facilitating payment for healthcare services and supplies; and 3) A web interface and transaction system for a healthcare service and supply interactive virtual marketplace, including healthcare service and supply product offerings, Point of Sale healthcare service and supply purchases, transaction data collection and analysis, payment collection, and distribution of payments.

Thus, herein are provided a plurality of embodiments the invention, including, but not limited to:

A method for using a computerized system for matching healthcare consumers to healthcare producers comprising the steps of:
  providing a producer interface to the system for each of a plurality of healthcare producers to interact with the system over the Internet;
  providing a consumer interface to the system for each of a plurality of healthcare consumers to interact with the system over the internet;
  accepting, via the producer interface, one or more available products and/or available services listings from each of a plurality of healthcare producers;
  accepting, via the consumer interface, a request from one consumer who is one of the plurality of consumers regarding a desired healthcare product or service;
  searching, using the system, the plurality of products and/or services listed by the plurality of producers for a subset of the products and/or services that are a close match to the requested healthcare product or service;
  providing a list of one or more items of the subset of products and/or services for display to the one consumer;
  offering the items on the list of items for purchase by the one consumer; and
  if the one or more of the offered items is accepted for purchase by the one consumer, performing the steps of:
  accepting payment information regarding the accepted purchase by the one consumer for the one or more items to be purchased;
  allocating a portion of the payment to the producer(s) corresponding to the purchased item(s); and
  allocating a remaining portion of the payment, if any, to a representative of the system.

Also provided is the above method further comprising the step of the system determining a quality assessment of one or more of the product(s) and/or service(s) purchased by the one consumer based on survey information obtained by the consumer.

Still further provided are any of the above methods further comprising the step of offering a transaction guarantee to the one consumer for purchase, wherein if the one consumer purchases the transaction guarantee and the quality assessment provides a determination that one or more of the one or more product(s) and/or service(s) purchased by the one consumer did not meet a quality threshold, at least a partial refund is provided to the one consumer.

Also provided are any of the above methods wherein the at least partial refund is at least partially deducted from the portion of the payment provided to the corresponding producer(s)

Further provided are any of the above methods wherein the step of offering the items on the list of items for purchase by the one consumer is accomplished via an auction process provided by the system, and wherein the one consumer is only offered the items for purchase if the one consumer wins the auction.

Further provided are any of the above methods wherein the system accepts full payment for the purchased items from the one consumer prior to the corresponding producer(s) actually delivering the product(s) and/or performing the service(s) that were purchased by the one consumer, such as where the portion of the payment allocated to the corresponding producer(s) is provided after the product or service has been provided by the corresponding producer(s), and optionally where the payment(s) are processed by a third-party payment processor.

In addition is provided any of the above methods, wherein a comprehensive HCS/S reference database is utilized during the searching step, wherein the database includes a plurality of the items from the list of items consisting of: symptoms associated with common medical conditions; operating characteristics and descriptions of common medical screening tests; Current Procedural Terminology (CPT) code definitions, and Healthcare Common Procedure Coding System HCPCS code definitions.

Further provided is method for using a system comprising computer equipment for matching healthcare consumers to healthcare producers comprising the steps of:
  providing a producer interface to the system for each of a plurality of healthcare producers to interact with the system over the Internet;
  providing a consumer interface to the system for allowing a consumer to interact with the system over the internet;
  maintaining, on the system, a quality assessment of a plurality of the plurality of producers;
  accepting, via the producer interface, one or more available products and/or available services listings each of the plurality of healthcare producers;
  accepting, via the consumer interface, a request from the consumer regarding a desired healthcare product or service;
  searching, using the system, the plurality of products and/or services listed by the plurality of producers for a subset of the products and/or services that are a close match to the requested desired healthcare product or service;
  providing a list of one or more items of the subset of products and/or services for display to the consumer;
  providing, when available, the quality assessment associated with each provider corresponding to each one of the one or more items for display to the consumer;
  offering the items on the list of items for purchase by the consumer; and
  if one or more of the offered items is purchased by the consumer, performing the steps of:
  accepting payment, using the system, from the consumer for the purchased item(s),
  after the product(s) or service(s) have been provided by the producer(s) corresponding to the item(s) purchased, providing, using the system, a portion of the payment to the corresponding producer(s),
  requesting, using the system, quality information from the consumer about each of the purchased items,
  updating, using the system and using the quality information, the quality assessment for each of the producers for which the consumer provided corresponding product or service quality information, and
  providing, using the system, a remaining portion of the payment, if any, to a representative of the system.

Also provided is a computerized system for implementing any of the above methods.

In addition, a system for matching healthcare consumers to healthcare producers is provided, with the system comprising:
  computer hardware resources; a web server using at least a portion of the computer hardware resources; a database using at least a portion of the computer hardware resources; a producer subsystem using at least a portion of the computer hardware resources and utilizing the web server and database for providing a producer interface for each of a plurality of healthcare producers using computers to interact with the system over the Internet, wherein the producer subsystem accepts from the producer computer(s), utilizing the web server and database, one or more available products and/or available services listings from each of the plurality of healthcare producers for storing in the database; and a consumer subsystem using at least a portion of the computer hardware resources and utilizing the web server and database for providing a consumer interface to the system for each of a plurality of healthcare consumers using computers to interact with the system over the internet.

The consumer subsystem of the above system accepts from at least one consumer computer, utilizing the web server and database, a request from one consumer regarding desired healthcare product or service, and at least a portion of the computer resources and information stored in the database are used for searching the plurality of products and/or services listed by the plurality of producers for a subset of the product(s) and/or service(s) that are a close match to the requested desired healthcare product or service.

The consumer subsystem of the above system is adapted for utilizing the web server and database for providing a list of one or more items of the subset of products and/or services for display to the one consumer on the one user computer for offering the items on the list of items for purchase by the one consumer; and when the system receives an indication from the user computer that one or more of the offered items is accepted for purchase by the one consumer, with the system being further adapted for using at least a portion of the computer hardware resources executing software for performing the steps of:

accepting payment information from the one consumer computer for the one or more purchased items;
  calculating a portion of the payment for providing to the producer(s) corresponding to the purchased product(s) and/or service(s); and
  calculating a remaining portion of the payment, if any, for providing to a representative of the system.

Also provided is the above system further comprising an administrative subsystem using at least a portion of the computer hardware resources and utilizing the web server and database for remotely connecting to system administrators using computers over the Internet.

Also provided are any of the above systems wherein the consumer subsystem obtains quality information about the corresponding producer(s) and/or about the one or more purchased items from the one consumer via the one consumer computer, and wherein the system, using the computer resources, maintains a quality assessment about the corresponding producer(s) based on the quality information provided by the one consumer and other consumers for storing in the database for association with the corresponding producer(s), and optionally where the quality assessment associated with the corresponding producers based on quality information previously provided by other consumers is provided to the one consumer, via the one consumer computer, along with the list of one or more items.

Further provided are any of the above systems wherein the consumer subsystem provides a transaction guarantee offer to the one consumer computer for purchase by the one consumer, wherein, if the system receives an indication that the consumer is purchased the transaction guarantee and the quality information provided by the consumer shows that one or more of the one or more product(s) and/or service(s) purchased by the one consumer did not meet a quality threshold, the system calculates at least a partial refund to be provided to the consumer.

In addition, provided are any of the above systems wherein the offering the items on the list of items for purchase by the one consumer is accomplished via an auction process provided by the system to the plurality of consumers, and wherein the one consumer is only offered the items for purchase if the one consumer wins the auction.

Further provided are any of the above systems wherein payments are accepted from the one consumer, and provided to the corresponding producer(s), using a third-party payment processor.

Also provided are additional embodiments of the invention, some, but not all of which, are described hereinbelow in more detail.

BRIEF DESCRIPTION OF THE DRAWINGS

The features and advantages of the examples of the present invention described herein will become apparent to those skilled in the art to which the present invention relates upon reading the following description, with reference to the accompanying drawings, in which.

DETAILED DESCRIPTION OF THE EXAMPLE EMBODIMENTS

Figure 1:
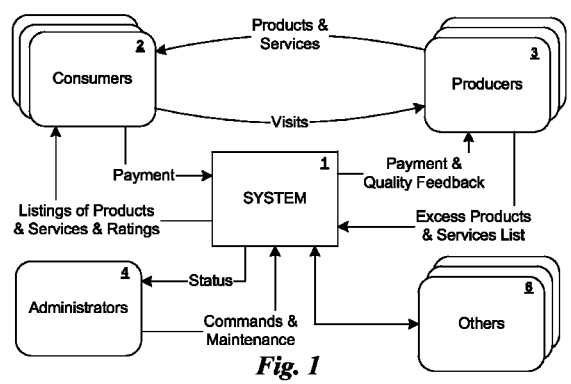
FIG. 1 shows a top-level diagram of an example embodiment of the system.

The Systems and Methods disclosed herein provide for an organized virtual marketplace transaction system for out-of-pocket HCS/S transactions. Healthcare consumers seek healthcare services and supplies in a highly regulated and complex marketplace, and healthcare producers sell healthcare services and supplies in a highly regulated and complex marketplace. Generally, the example system can be used as follows:

HCS/S Consumers use the System to search for, identify, and purchase healthcare services and supplies (HCS/S);
  HCS/S Consumers use the System to identify high quality healthcare service and supply Producers;
  HCS/S Consumers obtain high value healthcare services and supplies through the System;
  HCS/S Producers use the System to offer and to sell healthcare service and supplies; and
  Healthcare Producers sell HCS/S latent production capacity and excess inventory through the System.

The System can be used for conducting an interactive marketplace for healthcare services and supplies and organizing and facilitating payment for HCS/S, with the System of the example embodiment generally comprising: a web-based interface to post HCS/S availability and pricing information, the System posting HCS/S availability and pricing information, wherein product availability and pricing information represents healthcare services and supplies made available by healthcare service and supply Producers; and through which Consumers are able to purchase HCS/S; guaranteeing Point of Service payment for HCS/S, providing Point of Sale collection of payment from Consumers, collection of healthcare service and supply satisfaction data at Point of Service, analysis of Point of Service HCS/S satisfaction data and incorporation of said data analyses in development of relationships with Consumers and Producers.

An extension of the example system can provide an HCS/S Auction System, in addition to fixed cost payment systems. The example System can also be extended to include a Transaction Guarantee function through which the Consumer may purchase a guarantee of their subsequent satisfaction with the purchased HCS/S and providing Consumer refunds or partial refunds of Point of Sale payment for healthcare services and supplies that do not provide excellent Consumer satisfaction.

The example system (System) also includes software programs for executing on one or more servers for providing healthcare service and supply inventory management, healthcare service and supply purchase, sale, and sale confirmation. Furthermore, in support of quality control, healthcare service and supply satisfaction survey data collection and analysis functions are also provided. The System is basically implemented using a software program or programs maintained on a hardware server platform, with the software program(s) comprising: a marketing and inventory management software program and a user friendly graphical user interface, including healthcare service and supply inventory management, pricing and availability, sale and transaction closure subroutines; the hardware platform comprising co-located server(s) with secure encryption.

The software program and hardware platform of the System are preferably accessible through any web-enabled device, such as a personal computer connected to the Internet and running a commercially available operating system with a web browser. Through their personal computers connected to the System, Consumers buy healthcare services and/or supplies via the System from Producers, and Consumers evaluate services and supplies through a customer satisfaction survey process provided by the System. These Consumer data are collected and stored in a database on the System.

The database is analyzed by the System for variation and outcomes data to obtain quality assessments. Service and quality assessments are reported to Producers, Consumers and the company. The data is collected, stored, analyzed, and presented in a standard format to teach and guide Consumers and Producers to the healthcare purchasing and vending choices that best meet their needs. Producers are ranked into tiers based upon Consumer feedback and the evaluation of the Producers by the System.

System Overview

Broadly, the general purpose of the System 1 is shown by the generic high-level context diagram of FIG. 1, showing a current example embodiment of the system. The Consumers 2 seek healthcare services and supplies through the System 1, and the System 1 matches the Consumers 1 with the desired healthcare services and supplies, listed on the System 1 by the Producers 3. The healthcare Producers 3 offer healthcare services and supplies to Consumers 2 through the System 1, and the Producers 3 obtain revenue from the Consumers 2. The System 1 receives a commission for the matched services and/or supplies, and the System 1 provide revenue to the Producers 3. The Consumers 2 typically receive the services and supplies directly from the Producers 3, although the System 1 might aid in that as well. The System 1 is administered by System Administrator(s) 4 which interact with the System 1. The System 1 is basically owned, operated, and/or maintained by some person, organization, or entity (the "Company") that receives revenue from this process. The System Administrator(s) may be employees of the "Company", or third-party contractors paid for administering the System. Other entities 6 may use the system as well, such as contractors, insurance agents, evaluators, government entities, etc. Such use may be more limited, or different in function, than the other users and most of these are not described in any detail herein as being primarily of a peripheral nature to the operation of the system.

Users of the System 1 are thus the producers and consumers of healthcare services. Furthermore, the System Administrators 4 maintain, thereby using, the System. The basic goal of the system is to connect Producers 3 to Consumers 2 who otherwise might have difficulty finding each other. In essence:

a. Consumers—Are any user seeking healthcare supplies and services. They may be logged in as consumers, producers, system administrators, or neither to search the site. Producers and system administrators will be considered anonymous users and must create an account to complete the purchase;

b. Producers—Are users who have healthcare supplies or services to provide; and c. System Administrators—Have access to all data and information necessary to allow the system to run smoothly.

Figure 1A:
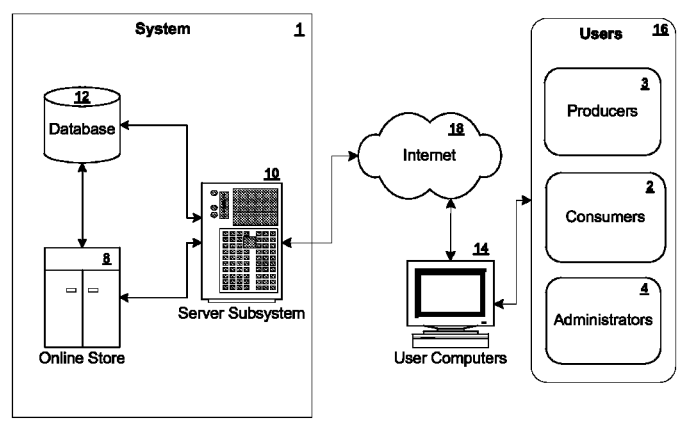
FIG. 1A is a diagram showing the example embodiment of the system in more detail.
Figure 1B:
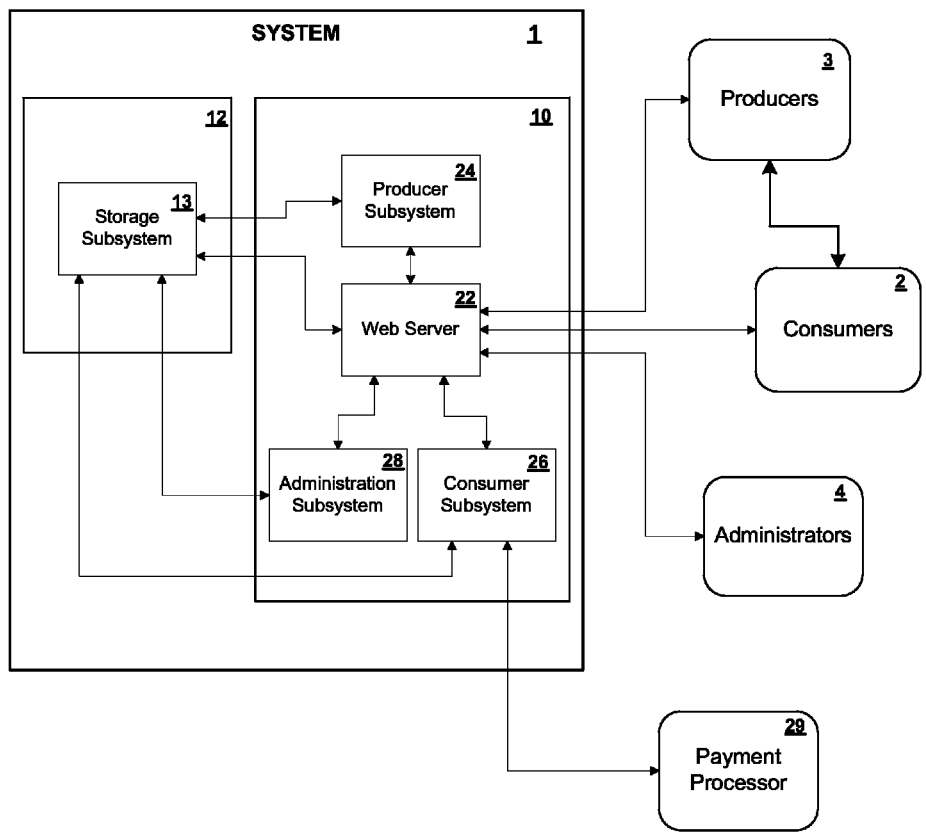
FIG. 1B is a diagram showing a breakdown of the example embodiment into subsystems.

FIGS. 1A and 1B show a system implementation of the example embodiment at a relatively high level, with the System 1 comprising a Server Subsystem 10, a Database 12, and an Online Store subsystem 8. The System 1 connects to the Users 16 via computer terminals or other web enabled devices 14 via a network 18, such as the Internet. FIG. 1B shows some of these subsystems in more detail, with the Server Subsystem 10 being broken out into a Web Server 22, a Producer Subsystem 24, a Consumer Subsystem 26, and an Administration Subsystem 28.

The Web Server 10 of the example embodiment can be generalized as a module that accepts requests from the Users 16 and provides the users with a response based on their request, and thus is the primary interface with the external world, although other interfaces can be utilized where appropriate.

The Producer Subsystem 24 can run on the web server hardware with the web server software, and acts as a GUI for the Producers 3 who are requesting data from the system. This subsystem interacts with the web server and the Database Subsystem 12 to provide any data requested by the Producers 3.

The Consumer Subsystem 26 of the example embodiment can also be made to run on the web server hardware and acts as a GUI for the Consumers 2 who are requesting data from the system. This subsystem interacts with the web server 22 and the Database 12 to provide any data requested by the Producer 3.

The Administration Subsystem 28 of the example embodiment can also be made to run on the web server hardware, and acts a GUI for the system administrators who are requesting data from the system. This subsystem interacts with the web server and the database server to provide any data requested by the system administrator.

The Database Subsystem 12 of the example embodiment is comprised of a Storage Subsystem 13 that can be considered a separate web server that stores all data that is accessed or requested by the consumers, producers, and system administrators. Of course, there are a number of additional database implementations known in the art that could be utilized for other embodiments.

The Payment Processor 29 of the example embodiment interacts with the User Subsystem 26, and can be an external entity, such as a credit card processing API on the internet. It can be considered inside or outside of the system boundary, but is part of the system process of the example embodiment, and is connected to via a curl request made by the Consumer Subsystem 26 from the Web Server 22.

Generally, the System 1 is comprised of one or more servers including one or more computers of various types that are known in the industry. For example, various computer hardware is available, such as that utilizing Intel processors that can operate using a Windows Server or Linux or another operating system. Such systems would typically include RAM memory, one or more hard drives, and one or more displays, mice, and/or keyboards. One or more database servers can also be utilized, which might be installed on the same computer hardware, or on separate hardware. As system utilization increases, additional hardware resources would be useful, and each primary application may have its own dedicated server, or may even be spread across multiple servers.

The system will require the use of various computing resources to perform some calculations and execute various software logic to implement the software subsystems. For example, payment calculations, quality performance parameters, and other values will be calculated by the system, as described below. The system can optionally also have an auction function, also described below, that will require the use of the computer resources. These computer resources can be shared with the various subsystems and servers (discussed above), such as the web server, database, and other subsystems, or dedicated computer resources could be utilized, if preferred, in any of a number of ways known by those skilled in the art.

Typically, these servers will be executing a commercially available software packages. For example, the web server would utilize such web server software such as MS IIS or Apache, extended through the use of one or more programming languages, such as C, C++, Java, etc. The system functions are thus implemented using one or more such programming languages, and the functions may execute on one of the servers, or could be executed on a client machine if the code is served with a web page, for example.

Commercially available database software can be utilized for the database(s), such as MS SQL Server, MySQL, Oracle, db4, etc. The database could be object oriented or relational. The servers and databases can be connected using the tools typically provided with the database, or third party applications, such as Java, C++, etc.

The System servers would be connected to the Internet in any of a number of known ways, and the System applications could also be installed on commercially available third-party server farms rather than on hardware owned by the System.

The terms "computer", "server", "computer network" or "network" as used herein should be broadly construed to include any device capable of receiving, transmitting and/or using information in the manner those terms are broadly understood by those skilled in the computing arts, including, without limitation, a processor, microprocessor or similar device, a personal computer such as a laptop, palm, PC, desktop or workstation, a network server, a mainframe, and an electronic wired or wireless device. Further, a computer, computer network, server, or network may operate in communication with other systems over any type of network, such as, for example, the Internet, an intranet, or an extranet, or may operate as a standalone system. Such networks may be implemented in using any of many different available types of communication schemes, such as those utilizing Ethernet, wireless, radio, cellular, fiber optics, etc. When the term "Internet" is sued, any appropriate computer network may be substituted, if desired.

The client computers can be any retail computer, laptop, server, mainframe, or netbook running a commercially available operating system (such as Windows XP, Windows 7, or other variants, of Windows; an Apple OS, Linux, or even a thin operating system such as Google Chrome OS), and having any of a number of web browsers installed (such as Internet Explorer, Firefox, Google Chrome, Netscape, etc.). Furthermore, PDAs and Smartphone's might also be utilized, in particular when they have the ability to interact with websites.

Furthermore, the various functions of the System, described below, will be organized into various subsystems that include software executing on hardware platforms. The hardware used by the various subsystems may be shared, or dedicated, depending on the expected utilization of the system. A heavily utilized system will require more hardware resources, and thus lend itself to dedicating computers/servers to various subsystems, whereas a less heavily utilized system may have all subsystems sharing the same hardware resources. Any of these implementations are within the scope of the example embodiments provided herein.

For example, referring again to FIG. 1B, a System 1 that interacts with many Consumers 2, but only a few Producers 3 and a limited number of Administrators 4, may have a dedicated server platform for executing the Consumer Subsystem, and another hardware platform for executing all of the Web Server 22, the Producer Subsystem 24, and the Administration Subsystem 28. A heavily utilized database may also require its own server. In contrast, a lightly used system may use a single server platform to execute all of these subsystems, whereas an extremely heavily utilized system may have a dedicated server (or even a server farm) for each of the subsystems.

Note that nothing prevents various users from having multiple roles, or roles that may change on occasion. For example, producers may, at some point, be consumers, for example, or vice versa.

For the example embodiment, the storage subsystem database main class and database structure and detailed class and database structure diagrams have detailed tables that can be directly implemented in any database. To create the database from the diagrams, refer only to the data elements. For this web based project the company has implemented the database structure using MYSQL and in this case server version 5.0.67.d7-ourdelta-log.

For the example embodiment, the website user interface can be created using nearly any programming language. Current implementations such as this are done using a server side programming language such as PhP to generate an html page that displays dynamic data from a MYSQL database. Any server side/client side implementation will work equally as well. The company chose an implementation that uses Adobe Flash, Adobe Flash Remoting, AMFPHP, PHP, and MySQL.

For the example embodiment, the backend administrative user interface can be created using a multitude of technologies. Any programming language that can be used to communicate with the chosen database implementation and manage that database can be used. For this embodiment it was chosen to implement the backend with PhP and MySQL.

The database implementation, web site user interface, and backend administrative user interface described above are all implemented on a web server in the example embodiment. For the software, server hardware, server operating system, and server implementation, any of the typical hardware/software combinations used in the web industry can be utilized. For the example implementation, a commercially available Go Daddy.com® hosting server with a Linux operating system and an apache server supply the desired basic platform, modified with customized software as discussed herein to implement the system.

System and Process Description

As discussed above, the System provides a web interface to users, including: a product offering and purchase function, data collection and analysis functions, and a payment collection and distribution functions. The System provides a healthcare matching service through which:

Healthcare services and supplies (HCS/S) are offered for sale;
Health information is made available to healthcare service and supply Consumers and Producers;
Healthcare services and supplies are purchased;
Receipts for healthcare services and supplies are provided to healthcare service and supply Consumers and Producers; and
Service and transaction satisfaction surveys are collected from healthcare Consumers.

Figure 2A:
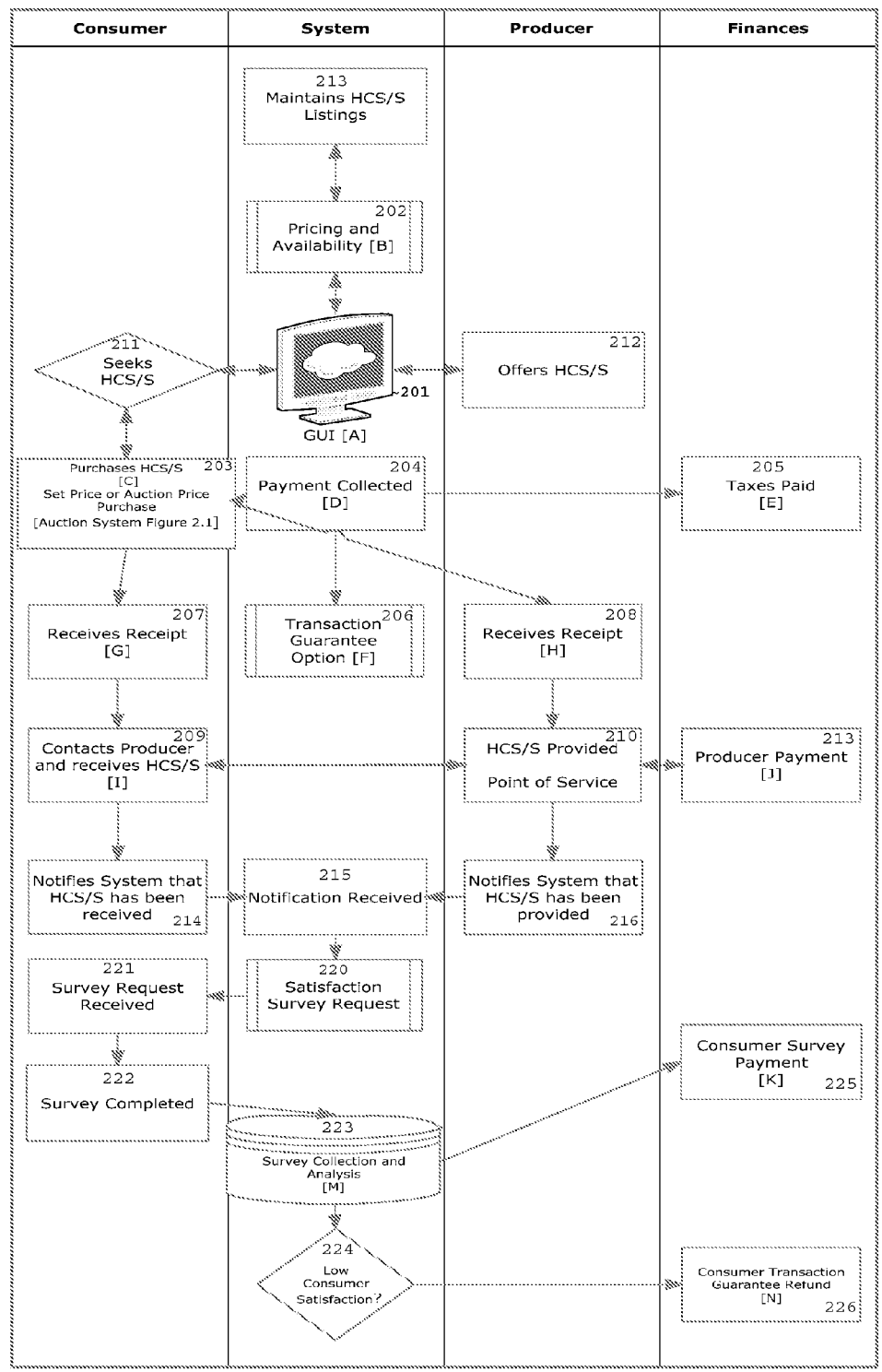
FIG. 2A shows a flowchart of one aspect of the example embodiment.

FIG. 2A shows the primary flow of functions of the System of the example embodiment for a standard payment process.

The System of the example embodiment utilizes a web interface including a graphical user interface (GUI) 201 accessible to all Web enabled functions. The GUI 201 provides HCS/S offering information 211 for HCS/S Consumers and HCS/S listing opportunities for HCS/S Producers 212.

The GUI 201 allows the System of the example embodiment to present HCS/S availability, quality and pricing information 202. HCS/S listings 213 are listed and described to the user (particularly to the Consumers) in user friendly 'layman's' terms. Product listings include date and time availability and physical location of HCS/S where applicable. HCS/S are offered for sale to the Consumers, typically for a set price or through an auction bidding process.

Consumers identify, select and purchase HCS/S through the GUI through secure web based transactions (Point of Sale purchases) 203.

The System of the example embodiment typically collects full HCS/S payment and full applicable sales taxes from the Consumer at Point of Sale 204. Sales tax(es) is/are then paid to the taxing entity or entities 205. At Point of Sale, the Consumer is offered a Transaction Guarantee 206 for purchase. The Transaction Guarantee provides the Consumer with a guaranteed refund of a portion of the purchase price if the Consumer is not sufficiently satisfied with the healthcare service or supply following Point of Service. The System presents Consumer and Producer transaction receipts at Point of Sale 207, 208. These receipts are stored in the System and may be retrieved by the Consumer or Producer at any time (or, in other embodiments, for a limited time) following the transaction. Authorization information (such as password/userID) ensuring that only authorized parties can access the data can be utilized. Various security certificates or even encryption methods known in the art could also be used where more secure transactions are desired.

Following Point of Sale, the Consumer contacts the Producer and obtains the purchased HCS/S 209, and the Consumer notifies the System 214 when the HCS/S is received 215 and/or the Producer notifies the system that the service has been provided 216. Producers are paid for healthcare services and supplies 213 at the time of delivery of the purchased HCS/S (Point of Service) 210.

As an extension of the example embodiment to ensure quality control and consumer and producer satisfaction, following Point of Service, Consumers are requested, and may be paid (225) or offered other compensation, to complete transaction specific quality surveys 220, 221, 222. These surveys collect Consumer satisfaction data for storage and are subsequently analyzed by the System 223. The results of the survey analysis are utilized to determine customer satisfaction 224, and identify high quality Producers. Consumer refunds can be provided for low satisfaction where applicable 226. Third party providers might be utilized for this surveying process in some alternative embodiments.

Figure 2B:
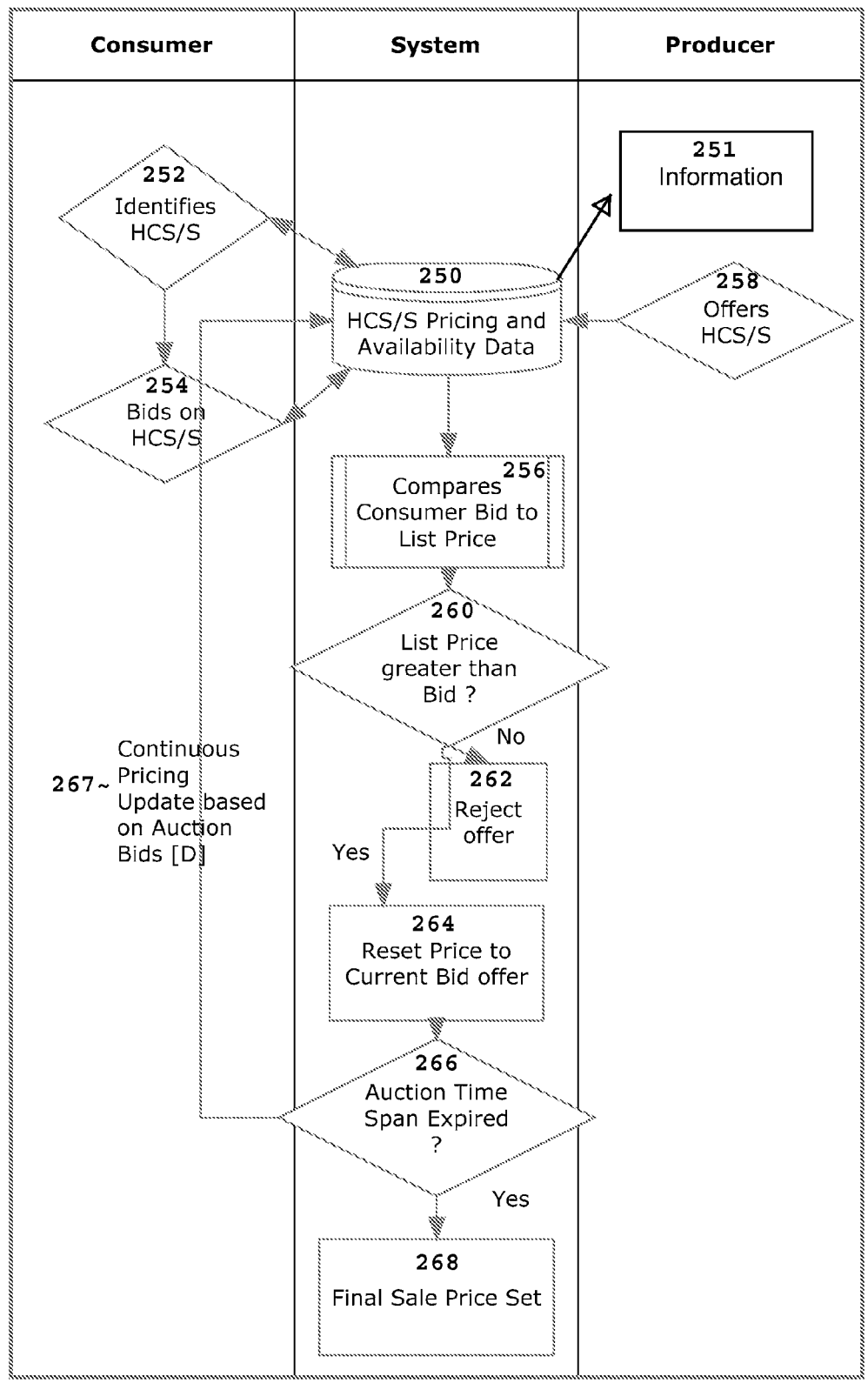
FIG. 2B shows another flowchart of another aspect of the example embodiment.

FIG. 2B shows the example System modified to add auction support as a payment option. The Auction System maintains HCS/S product information 250 and provides HCS/S Producers 251 and Consumers 252 real time access to this information. The Auction System receives bids for HCS/S based on the Minimum Bid Price of the HCS/S of interest 254. The Auction System compares the bid to the list price 256, and sets the HCS/S price at the higher of: the HCS/S Minimum Bid Price or the HCS/S bid price 260, 262, 264. The Auction System continuously updates the price of the HCS/S of interest 267, and Producers can monitor this information 258. The Final Sale Price 268 is set at termination of the Auction Time Span 266. HCS/S may also be purchased at the 'Purchase Now Price' set by the HCS/S Producer. HCS/S purchased at the 'Purchase Now Price' are transacted through the standard set price purchase process.

The Database of the example embodiment tracks and compiles transaction and Producer data. Producers are scored and ranked according to quality scores and transaction data analyses, collected such as described above. These data are used to establish Producer membership tiers with associated rewards systems. Consumer memberships are linked to product discount offerings, monetized volume incentives and discounted pricing. Producer memberships are linked to increased reimbursement for high Consumer generated Producer scores.

In an extension of the example System, a live 'chat' function can be provided through which the Consumer communicates with HCS/S Producers. Consumers and HCS/S Producers discuss Consumers' HCS/S needs. Such a function may utilize administrators (or another external entity not shown) provided for that purpose.

The System of the example embodiment can also be extended to provide a comprehensive HCS/S reference database stored in the Database, including: symptoms associated with common medical conditions; operating characteristics and descriptions of common medical screening tests including capabilities and costs; CPT (Current Procedural Terminology) and HCPCS (Healthcare Common Procedure Coding System) code definitions; and HCS/S providers availability, quality and cost comparison data.

Producers can list items for sale through the system for matching with consumers looking for those items.

The System of the example embodiment preferably stores all Consumer and Producer information on a secure server. The Company may access, analyze and modify this information at the Company's discretion.

In this example System, there are three basic types of users supported, as discussed above, known as Producers 3, Consumers 2, and System Administrators 4 (although other entities may be considered additional users, such as "Company" representatives, tax entities, suppliers, etc.). As discussed above, the basic goal of the system is to connect Producers 3 to Consumers 2 and obtain reasonable revenue based on that connection. Finally, non-categorized users may be exploring the site. Thus, users may be logged in as consumers, producers, system administrators, or none of these to search the site. Producers and system administrators can be considered anonymous users. Users must create an account to complete a purchase, and there may be an authorization process, connection to financial accounts, and other procedures to ensure that fraudulent use of the System is minimized.

Consumers are basically those users seeking healthcare supplies and/or services; Producers are those users who have healthcare supplies or services to provide (and thus are seeking consumers for those supplies and/or services); and System Administrators are those users who have access to all data and information necessary to allow the system to run smoothly and help maintain the system.

Referring back again to FIG. 1B, in this example System 1, the Web Server 22 can be generalized as a terminal that accepts requests from clients and provides the client with a response based on their request, and is implemented using a commercialized web server platform. The Producer Subsystem 24, Consumer Subsystem 26, and Administration Subsystem 28, all run on the web server platform and act as GUIs for the respective users.

The Storage Subsystem 13, in contrast, can be a separate web server or database subsystem that stores all or most of the data that is accessed or requested by the consumers, producers, and system administrators. These subsystems therefore provide the features discussed below through detailed programming of these subsystems as software programs executing on the system hardware that was discussed above.

Example System Implementation Overview

System implementation and functionality is provided in more detail in this section. [Note: In this section and the cited Figures, Data Elements are shown as <—data element> and Methods are shown as <+method> as used in standard UML class diagrams.]

Figure 3A:
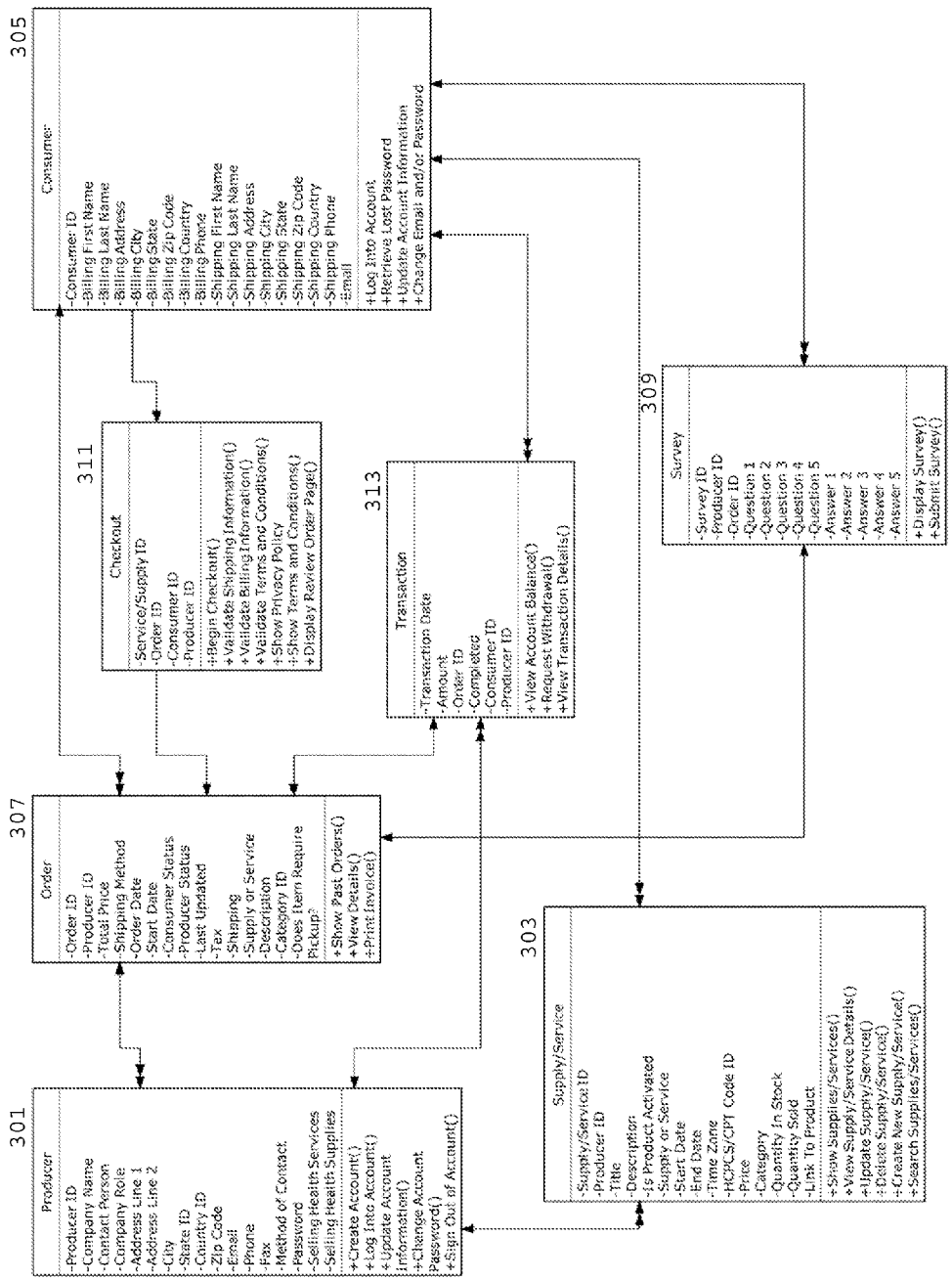
FIG. 3A shows the Main Class and Database Structure of the example embodiment.
Figure 3B:
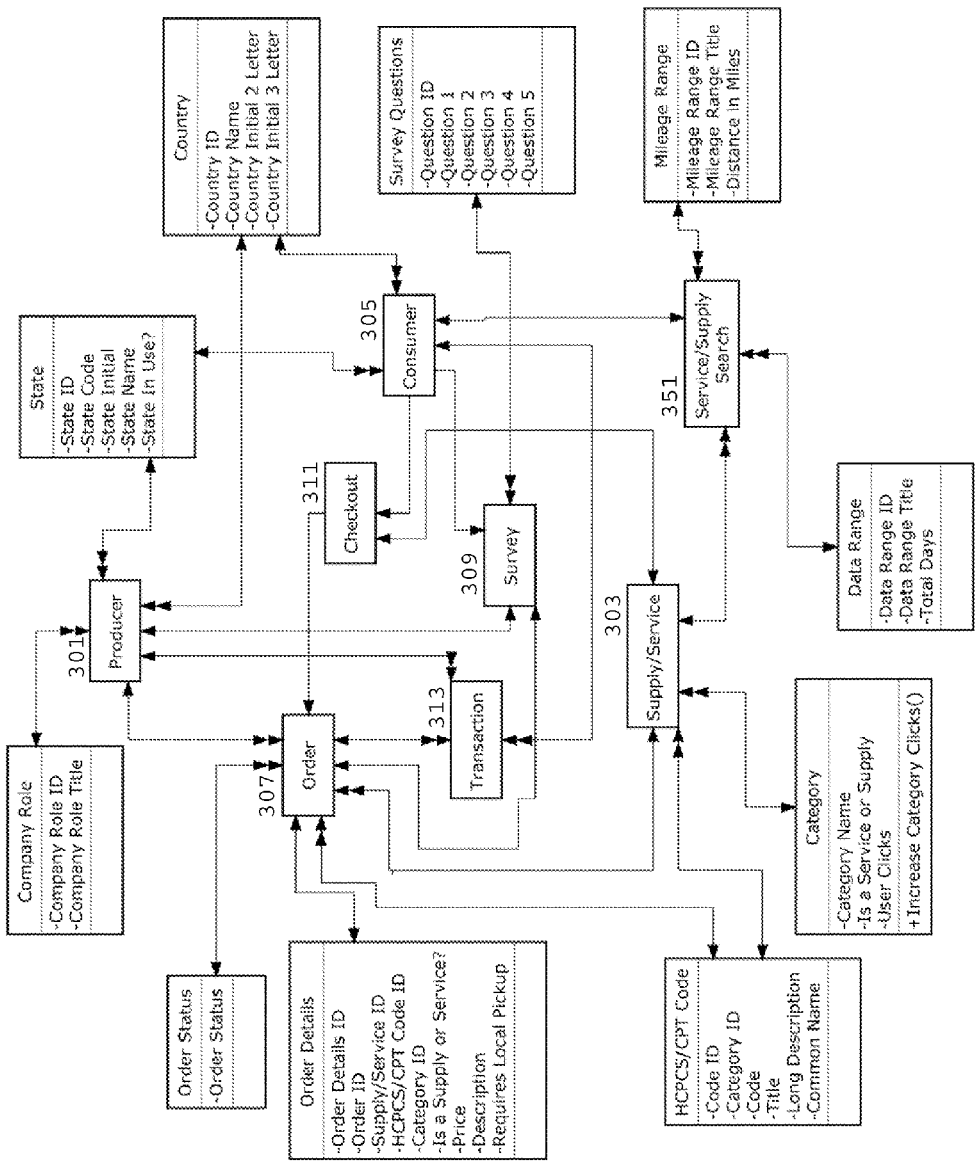
FIG. 3B, shows a Detailed Class and Database Structure of the example embodiment.

User Interface:

The user interface is comprised of a series of lists, forms, text fields, and other display techniques that implement several classes that consist of data elements and methods. The data elements and methods are abstracted to a level that can be applied to all object oriented programming languages. The user interface is accessible by producers, consumers, and/or anonymous users and depending on their access level can view different portions of the interface. These items should be read in light of the relationships between them shown in FIG. 3A, showing the Main Class and Database Structure of the example embodiment, and FIG. 3B, showing a Detailed Class and Database Structure.

For the example embodiment, the user interface is primarily provided by the Web Server 22, interacting with the respective subsystems for serving information to the user computers.

There are six primary parts of the user interface to be implemented by the software design, the general features of which are summarized as follows:

I. Producer

References the producer class in the main structure;

The company role field is a foreign key connecting the producer to the company role table in the database. By connecting this field to a database table it allows the company to add and remove company roles throughout the system;

The state field is a foreign key connecting the producer to the state table in the database. By connecting this field to a database table it allows the company to add and remove states, provinces, or territories throughout the system;

The country field is a foreign key connecting the producer to the country table in the database. By connecting this field to a database table it allows the company to add and remove countries throughout the system;

The producer is connected to the transaction database. Each transaction stores the producer id that is connected to that transaction;

The producer is connected to the order database. Each order stores the producer id that is connected to that order;

A producer is connected to the survey table. Every survey is a review of a producer and references the producer through the survey's producer id.

II. Order

References the order class in the main structure;

The order stores additional data in an order details table. The order details uses an order id foreign key to attach the order's details to the order;

The order has an order status that must be listed in the order status table. This allows the company to add and remove order status's throughout the entire system;

The order can be connected to multiple transactions. Each transaction stores an order id to reference the order table. The order may have a transaction to add to the producer's balance upon a sale or a transaction to show the credit to a consumers account for a service guarantee or a survey refund;

An order can be referenced to a survey through a foreign unique key stored in the survey;

An order references an HCPCS/CPT code through a foreign key that is stored in the HCPCS/CPT Code id field of the order;

An order references a particular producer through a foreign key that is stored in the producer id field in the order;

An order references a particular consumer through a foreign key that is stored in the consumer id field in the order;

An order does not reference a particular supply/service. Instead all important information of the particular supply/service is saved to the order. The reason for this is that a supply/service information could be changed by the producer or the company and we do not want this change reflected in the order that was placed by the consumer.

III. Consumer

References the consumer class in the main structure;

The state field is a foreign key connecting the consumer to the state table in the database. By connecting this field to a database table it allows the company to add and remove states, provinces, or territories throughout the system. The state table is the same state table for the producer, simply duplicated for readability;

The country field is a foreign key connecting the consumer to the country table in the database. By connecting this field to a database table it allows the company to add and remove countries throughout the system. The country table is the same country table for the producer, simply duplicated for readability;

A consumer can search for and find a supply/service using the service/supply search class;

A consumer is connected to the transaction database. Each transaction stores the consumer id that is connected to that transaction;

A consumer can insert a survey into the survey table. Once inserted the consumer is no longer connected to the survey that they created. This allows for an anonymous review of a producer;

A consumer can use the check out class to complete a purchase of a service/supply which is found using the service/supply search class.

IV. Survey

References the survey class in the main structure;

When a new survey instance is created the current survey questions are pulled from the survey questions table. The survey questions that are asked are saved to the survey database along with the answers;

Each survey references a producer through the producer id which is saved to the producer id field;

Each survey references an order through the order id which is saved to the order id field.

V. Transaction

References the transaction class in the main structure;

Each transaction references one producer or consumer and one order through their unique IDs;

A transaction cannot reference both a producer and a consumer.

VI. Supply/Service

References the supply/service class in the main structure;

Each supply/service references a particular code in the HCPCS/CPT code table through a unique code id. The code makes it easy and reliable for producers to create a service/supply with correct medical information attached;

Each supply/service references a category from a table of categories that are generated by the company.

The functions and features of these user interfaces are discussed in more detail in the following sections:

Producer Interface Data Elements & Methods:

These functions are provided primarily by the Producer Subsystem operating in conjunction with the Web Server and Storage Subsystem. Item 301 of FIG. 3A shows Producer user interface data elements and corresponding methods. Table 1 shows these methods (functions) with their conditions:

TABLE 1

Producer User Interface Methods

| | |
|---|---|
| +Create Account | Pre-conditions: The application form to create a new producer account is completely filled out with no errors. Post-conditions: The application data is submitted to the producer database to await activation by the company. A message is displayed to the user showing that the application was submitted. |
| +Sign into Account | Pre-conditions: The sign in form has a valid email address and the password field is not blank. Post-conditions: If the email matches the password in the producer database and the producer's account has been activated by the company, then the producer is logged into the system and shown their account page. |
| +View Account Information | Pre-conditions: The user is logged into their account. Post-conditions: The user's account information is displayed in a readable format. |
| +Update Account Information | Pre-conditions: The user is logged into their account and appropriate corrections have been made to their account information on their view account information page. Post-conditions: The user's account information has been saved to the database. |
| +Change Password | Pre-conditions: The user is logged into their account and they have entered a valid password into the password field. Additionally the first password must match the password in the password again field. Post-conditions: The user's password has been encrypted and saved to the database. |
| +Sign Out | Pre-conditions: The user is logged into their producer account. Post-conditions: The user has been logged out of their account. |

Supplies & Services Interface Data Elements & Methods:

Item 303 of FIG. 3A shows Supply/Service interface data elements and corresponding methods. Table 2 shows these methods (functions) with their conditions:

TABLE 2

Supply/Service Interface Methods

| | |
|---|---|
| +Show Supplies/Services (Producer) | Pre-conditions: The user has logged into their producer account. Post-conditions: The supplies/services that have been listed by the producer are displayed in a readable format. |
| +View Supply/Service Details | Pre-conditions: Somewhere in the system a supply/service was displayed in a clickable version that allows the user to click the item/link to view details. Post-conditions: The selected supply/service is displayed in a readable format. Appropriate buttons and links are displayed to allow a user to update, delete, purchase, or other actions depending on the user's credentials (Consumer, Producer, or Anonymous). |

TABLE 2-continued

Supply/Service Interface Methods

| | |
|---|---|
| +Create New Supply/Service (Producer) | Pre-conditions: The user has logged into their producer account, chose to create a new supply/service, and has correctly filled out the new supply/service form with valid input. Additionally, the system requires the producer to double check their input by displaying the product as it will be displayed to the consumer before saving it to the database.<br>Post-conditions: The new supply/service has been added to the database. If the producer has automatic supply/service activation credentials, then the product will immediately be available to purchase, otherwise the product will need to be activated by the company first. The product will be available for edits and to be removed in the producers supplies/services account page. |
| +Edit Supply/Service (Producer) | Pre-conditions: The user has logged into the producer account, has chosen a supply/service to edit, and has made appropriate corrections to the supply/service.<br>Post-conditions: The changes made to the supply/service have been saved to the database. |
| +Delete Supply/Service (Producer) | Pre-conditions: The user has logged into their producer account and has selected the product to delete.<br>Post-conditions: The product has been removed from the system. |

Consumer User Interface Data Elements & Methods:

These functions are provided primarily by the Consumer Subsystem operating in conjunction with the Web Server and Storage Subsystem. Item 305 of FIG. 3A shows Consumer user interface data elements and corresponding methods. Table 3 shows these methods (functions) with their conditions:

TABLE 3

Consumer User Interface Methods

| | |
|---|---|
| +Log into Account | Pre-conditions: The user has entered their email and password into the sign in form.<br>Post-conditions: If the entered values for the email and password match the values in the database then the user is logged in and can access their account information. If the entered values do not match the values in the database, then the user is given an appropriate error message. |
| +Retrieve Lost Password | Pre-conditions: The user has navigated to the "forgot my password" page and filled out the appropriate information required to reset their password.<br>Post-conditions: A random encrypted password is generated and emailed to the user and the encrypted password is saved to the database. |
| +Update Account Information | Pre-conditions: The user has logged into their consumer account and navigated to the account information form. The user has also updated the values in the form with valid inputs.<br>Post-conditions: The user's consumer account information has been saved to the database. |
| +Change Email and/or Password | Pre-conditions: The user has logged into their consumer account and has navigated to the change email and password page and have entered valid values for the email and password fields and the password and password again fields match.<br>Post-conditions: The new email and/or password has been saved to the users record in the database. |
| +Sign out from Account | Pre-conditions: The user has logged into their consumer account.<br>Post-conditions: The user is now logged out of their consumer account. |
| +Create New Account | Pre-conditions: The user has entered a valid email and password and the password and password again fields match. Additionally, the user is required to enter valid inputs for all fields in the address information form.<br>Post-conditions: The new consumer account is created and saved to the database. The user is now logged into their consumer account. |

Order Interface Data Elements & Methods:

These functions are provided primarily by the Consumer Subsystem operating in conjunction with the Web Server and Storage Subsystem. Item 307 of FIG. 3A shows Order interface data elements and corresponding methods. Table 4 shows these methods (functions) with their conditions:

TABLE 4

| Order Interface Methods | |
| --- | --- |
| +Display Past Orders | Pre-conditions: The user has logged into either their consumer or producer account. Post-conditions: If the user is viewing their consumer account then all orders that they have placed will be displayed in a readable format. If the user is viewing their producer account then all orders placed for your listed products will be displayed in a readable format. |
| +Display Order Details | Pre-conditions: The user has logged into either their consumer or producer account and has displayed a list of their previous orders and has clicked a specific order. Post-conditions: The selected order is displayed in a readable format. |
| +Print Order Invoice | Pre-conditions: The user has logged into either their consumer or producer account and has displayed a list of their previous orders and has clicked a specific order and clicked the print invoice link. Post-conditions: An invoice is generated for the order and sent to the user's printer for printing. |
| +Confirm Completed Service/ Supply | Pre-conditions: The user has logged into their consumer or producer account and has navigated to the correct order in their account. Post-conditions: If the user is logged into their consumer account then the consumer status data value is updated to show that the user has received their supply/service. If the user is logged into their producer account then the producer status data value is updated to show that the user has distributed the supply/service. |

Surveys Interface Data Elements & Methods:

These functions are provided primarily by the Consumer Subsystem operating in conjunction with the Web Server and Storage Subsystem. Item 309 of FIG. 3A shows Order interface data elements and corresponding methods. Table 5 shows these methods (functions) with their conditions:

TABLE 5

| Survey Interface Methods | |
| --- | --- |
| +Display Survey | Pre-conditions: The user has logged into their consumer account, selected a completed order from a list of displayed orders, and selected to take the survey. Post-conditions: The survey is displayed in a readable format. The survey questions can be static or can be pulled from the a survey question table in the database. |
| +Submit Survey | Pre-conditions: The user has logged into their consumer account, selected a completed order from a list of displayed orders, selected to take a survey, and answered every question in the survey. Post-conditions: The survey answers and corresponding order id and producer id are saved to the database and the consumer's credit card is credited for the survey payout amount. |

Checkout Interface Data Elements & Methods:

These functions are provided primarily by the Consumer Subsystem operating in conjunction with the Web Server and Storage Subsystem. A storefront subsystem might also be utilized. Item 311 of FIG. 3A shows Checkout interface data elements and corresponding methods. Table 6 shows these methods (functions) with their conditions:

TABLE 6

| Checkout Interface Methods | |
| --- | --- |
| +Begin Checkout | Pre-conditions: The user should have selected the supply/service that they would like to purchase. Post-conditions: The selected supply/service is added to the cart. |
| +Display Order Details | Pre-conditions: The user has selected a supply/service to purchase Post-conditions: The selected supply/service is displayed in a readable format and appropriate links and buttons are displayed to allow the user to continue in the checkout process. |
| +Display Shipping Information Page | Pre-conditions: The user has selected a supply/service to purchase and has successfully entered valid information in the previous checkout pages. Post-conditions: The shipping information page is displayed in a readable format with text fields for the user to enter their information. If their account has any shipping information saved, the text fields will be automatically filled in for the user. |
| +Display Billing Information Page | Pre-conditions: The user has selected a supply/service to purchase and has successfully entered valid information in the previous checkout pages. Post-conditions: The billing information page is displayed in a readable format with text fields for the user to enter their information. If their account has any billing information saved, the text fields will be automatically filled in for the user. |
| +Display Terms and Conditions Page | Pre-conditions: The user has selected a supply/service to purchase and has successfully entered valid information in the previous checkout pages. Post-conditions: The terms and conditions page is displayed in a readable format.' |
| +Display Terms and Conditions | Pre-conditions: None Post-conditions: The terms and conditions for the site is displayed to the user in a readable format. |
| +Display Privacy Policy | Pre-conditions: None Post-conditions: The privacy policy is displayed to the user in a readable format. |
| +Display Order Information and Final Price Details | Pre-conditions: The user has selected a supply/service to purchase and has successfully entered valid information into all previous checkout pages. |

TABLE 6-continued

Checkout Interface Methods

| | |
|---|---|
| | Post-conditions: The order information and final price details are displayed to the user and appropriate links are give to allow the user to make corrections or finalize the purchase. |
| +Display Order Completion Information | Pre-conditions: The user has selected a supply/service to purchase, successfully entered valid data to all checkout pages, and has confirmed the purchase of the supply/service. Post-conditions: The status of the order is displayed according to the results provided by the credit card processor. |
| +Validate Shipping Information | Pre-conditions: The user has selected a supply/service to purchase. Post-conditions: If the data is all valid then the user is taken to the next checkout page. |
| +Validate Billing Information | Pre-conditions: The user has selected a supply/service to purchase. Post-condition: If the data is all valid then the user is taken to the next checkout page. |
| +Validate Terms Agreement Box | Pre-conditions: The user has selected a supply/service to purchase. Post-conditions: If the user has checked the "I agree to the terms and conditions" box then the user is taken to the next checkout page, otherwise an appropriate error is displayed. |

Transaction Interface Data Elements & Methods:

These functions are provided primarily by the Producer Subsystem operating in conjunction with the Web Server and Storage Subsystem. Item 313 of FIG. 3A shows Transaction interface data elements and corresponding methods. Table 7 shows these methods (functions) with their conditions:

TABLE 7

Transaction Interface Methods

| | |
|---|---|
| +Show Account Balance Page (Producers) | Pre-conditions: The user has logged into their producer account. Post-conditions: The transactions are totaled with credits being positive and debits being negative and the total is displayed along with a list of each transaction. |
| +Request Withdrawal (Producers) | Pre-conditions: The user has logged into their producer account, entered a value into the amount to withdraw text field, and that amount is less than or equal to the total account balance. Post-conditions: The withdrawal amount is entered into the debit field, and a transaction is created to represent this. The transaction complete field is set to false or 0 until the company distributes the money to the user's bank account. |
| +Show Transaction Details (Producers) | Pre-conditions: The user is logged into their producer account and has selected a transaction from a list of all transactions. Post-conditions: The details of the transaction are displayed in a readable format. |
| +Credit Consumer Account (Consumers) | Pre-conditions: The user may have either completed an order and the survey associated with the order or has asked for money back on an order with a service guarantee. Post-conditions: The system requests a refund for the consumer through the credit card processor. The refund is given (based on the reason for the refund) to the user's credit card for the credit amount as determined by the system. |

Service/Supply Search Interface methods (functions) relationships are shown as item 351 in FIG. 3B and include the methods those shown in Table 8, and are provided primarily by the Consumer Subsystem operating in conjunction with the Web Server and Storage Subsystem:

TABLE 8

Supply/Service Search Interface Methods

| | |
|---|---|
| +Service/Supply Search | Pre-conditions: The user has entered all required search criteria. Post-conditions: All supplies/services relative to the search criteria are returned. Search algorithms will change as the size of the supplies/services database grows. If a small number of results are found the algorithm should find similar results to give the user that may help them find a useful supply/service. |
| +Display Search Results | Pre-conditions: The user has started a service/supply search and it has returned results to the display method. Post-conditions: The search results are displayed in a readable format with items that can be clicked for more details. |

TABLE 8-continued

| Supply/Service Search Interface Methods | |
|---|---|
| +View Result Details | Pre-conditions: The user has successfully searched the system for supplies/services and has clicked one of the results. Post-conditions: The selected result details are shown in a readable format. Relative links are provided to allow the user to purchase the supply/service. |

Site Administration:

The site administration can be created using any language that can connect to a database and display the data in a way that can be edited and saved back the database. The administration site serves as the backend for all data and a simple useful way for the company to manage the consumers, producers, and the data associated with them. These functions are provided primarily by the Administration Subsystem operating in conjunction with the Web Server and Storage Subsystem. [Note: The following Table 9 provides a list of methods that are used to implement the site administration. They connect to the database and relate to the data that is listed in the front end site documentation.]

TABLE 9

| Site Administration Methods | |
|---|---|
| Restrict Administrative Access and Redirect User to Log in Page | Pre-conditions: The user has attempted to access any page in the administrative site without first logging themselves into their administrative account. Post-conditions: The user is sent to the log in page and given a message that tells them that they do not have access to that page. |
| Log into Account | Pre-conditions: The user has entered their email and password for their corresponding administrative account. Post-conditions: The user is either sent to the web page that they were attempting to access last or the home page of the administrative site. The user now has access to the entire administrative site until they log out or their session expires. |
| Show Orders | Pre-conditions: The user is logged into their administrative account. Post-conditions: All orders that have been placed are displayed in a readable format. |
| Sort Orders by Time Period | Pre-conditions: The user is logged into their administrative account. Post-conditions: The list or orders are redisplayed as a sorted list by a time period, e.g. today's orders, yesterday's orders, the last week's orders, etc . . . |
| Sort Orders by Month and Year | Pre-conditions: The user is logged into their administrative account. Post-conditions: The list of orders are redisplayed as a sorted list by specific month and year. |
| Show Order Details | Pre-conditions: The user has logged into their administrative account and has selected a specific order to view. Post-conditions: The selected order is displayed in a readable format with all available details including available producer and consumer information connected to the order. |
| Delete Order | Pre-conditions: The user is logged into their administrative account and has selected an order to be deleted. Post-conditions: The selected order is removed from the system. |
| Show Transaction History | Pre-conditions: The user is logged into their administrative account. Post-conditions: All transactions are displayed in a readable format. |
| Sort Transactions by Time Period | Pre-conditions: The user is logged into their administrative account. Post-conditions: The list or transactions are redisplayed as a sorted list by a time period; e.g. today's transactions, yesterday's transactions, the last week's transactions, etc . . . |
| Sort Transactions by Month and Year | Pre-conditions: The user is logged into their administrative account. Post-conditions: The list of transactions are redisplayed as a sorted list by specific month and year. |
| Show Transaction Details | Pre-conditions: The user has logged into their administrative account and has selected a specific transaction to view. Post-conditions: The selected transaction is displayed in a readable format with all available details including available producer and consumer information connected to the transaction. |
| Delete Transaction | Pre-conditions: The user is logged into their administrative account and has selected a transaction to be deleted. Post-conditions: The selected transaction is removed from the system. |
| Show Products | Pre-conditions: The user is logged into their administrative account. |

TABLE 9-continued

Site Administration Methods

| | |
|---|---|
| | Post-conditions: All products that have been created are displayed in a readable format. |
| Show Product Details | Pre-conditions: The user has logged into their administrative account and has selected a specific product to view.<br>Post-conditions: The selected product is displayed in a readable format with all available details including available producer information connected to the product. |
| Activate Product | Pre-conditions: The user is logged into their administrative account and a product was selected to activate.<br>Post-conditions: The selected product is set to activated. |
| Delete Product | Pre-conditions: The user is logged into their administrative account and a product was selected to delete.<br>Post-conditions: The selected product is deleted from the system. |
| Show HCPCS/CPT Codes | Pre-conditions: The user is logged into their administrative account.<br>Post-conditions: All HCPCS/CTP are displayed in a readable format. |
| Sort HCPCS/CPT Codes by Code | Pre-conditions: The user has logged into their administrative account and has entered a part of or all of a code to search for.<br>Post-conditions: The list of HCPCS/CPT codes are redisplayed as a sorted list of HCPCS/CPT codes ordered by the most relative results and based on the entered code name. |
| Sort Codes by Title | Pre-conditions: The user has logged into their administrative account and has entered a part of or all of a title to search for.<br>Post-conditions: The list of HCPCS/CPT codes are redisplayed as a sorted list of HCPCS/CPT codes ordered by the most relative results and based on the entered title. |
| Sort Codes by Category | Pre-conditions: The user has logged into their administrative account and has selected a category of codes to view.<br>Post-conditions: The list of HCPCS/CPT codes are redisplayed as a list of HCPCS/CPT codes that fall under the selected category. |
| Update Code Information | Pre-conditions: The user has logged into their administrative account, has selected a specific code to made updates, and has made appropriate updates to the code information.<br>Post-conditions: The changes made to the selected code information are saved to the database. |
| Delete Code | Pre-conditions: The user has logged into their administrative account and has selected a code to be deleted.<br>Post-conditions: The code has been removed from the database. |
| Show Administrative Accounts | Pre-conditions: The user has logged into their administrative account.<br>Post-conditions: The administrative accounts are displayed in a readable format. |
| Show Producer Accounts | Pre-conditions: The user has logged into their administrative account.<br>Post-conditions: The producer accounts are displayed in a readable format. |
| Show Consumer Accounts | Pre-conditions: The user has logged into their administrative account.<br>Post-conditions: The consumer accounts are displayed in a readable format. |
| Add New Administrative Account | Pre-conditions: The user has logged into their administrative account and has filled in all required fields in the "create a new administrative account" form.<br>Post-conditions: A new administrative account is added to the database. |
| Add New Producer Account | Pre-conditions: The user has logged into their administrative account and has filled in all required fields in the "create a new producer account" form.<br>Post-conditions: A new producer account is added to the database. |
| Add New Consumer Account | Pre-conditions: The user has logged into their administrative account and has filled in all required fields in the "create a new consumer account" form.<br>Post-conditions: A new consumer account is added to the database. |
| Update Administrative Account | Pre-conditions: The user has logged into their administrative account and has made appropriate changes to the selected administrative account.<br>Post-conditions: The selected administrative account's changes have been saved to the database. |
| Update Producer Account | Pre-conditions: The user has logged into their administrative account and has made appropriate changes to the selected producer account.<br>Post-conditions: The selected producer account's changes have been saved to the database. |
| Update Consumer Account' | Pre-conditions: The user has logged into their administrative account and has made appropriate changes to the selected consumer account. |

TABLE 9-continued

Site Administration Methods

| | |
|---|---|
| | Post-conditions: The selected consumer account's changes have been saved to the database. |
| Delete Administrative Account | Pre-conditions: The user has logged into their administrative account and has selected an administrative account to delete. Post-conditions: The selected administrative account is removed from the database. If the user deleted the account that they are currently logged into then they are immediately logged out. |
| Delete Producer Account | Pre-conditions: The user has logged into their administrative account and has selected a producer account to delete. Post-conditions: The selected producer account is removed from the database. |
| Delete Consumer Account | Pre-conditions: The user has logged into their administrative account and has selected a consumer account to delete. Post-conditions: The selected consumer account is removed from the database. |
| Update Site Rates | Pre-conditions: The user has logged into their administrative account and has made appropriate changes to the site rates in the site rates form. Post-conditions: The changes to the site rates are saved to the database. |
| Show Site Reports | Pre-conditions: The user has logged into their administrative account. Post-conditions: All available reports for the status of the site are displayed. |
| Update General Site Settings | Pre-conditions: The user has logged into their administrative account and has made appropriate changes to the site settings. Post-conditions: Any changes made to the site settings are saved to the database. |

Example System Detailed Functional Description

Figure 4:
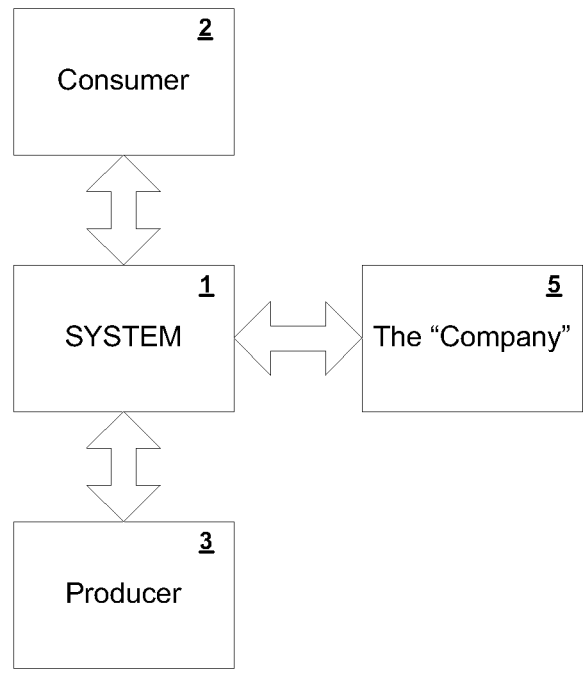
FIG. 4 shows a top-level flow relationship between various entities interacting with the example system.

The basic flow of information through the system is shown in FIG. 4. Basically, the System 1 interacts with the Consumer 2, the Producer 3, and The "Company" 5 which runs, owns, operates, or otherwise maintains (or all of these) the System 1 and receives the proceeds (profit) from the system.

The System 1 provides the Consumer 2 (using a computer connected to the System via a computer network) with the option of searching the System 1 for either a healthcare service or a healthcare supply. The System 1 provides the Consumer 2 with categories of healthcare service or supply for his selection, and allows the Consumer 2 to and search the category for available products of Producers 3 that are entered in the System 1. The Consumer 2 indicates his geographic location to the System 1 by entering his postal (zip) code and the distance range for the healthcare service or supply search into the System 1. For healthcare service searches, the Consumer 2 enters the preferred date of service and the date range for the preferred day of service.

The System 1 uses its stored data and the Consumer 2 inputs to present the Consumer 2 with a list of healthcare supplies and/or services that meet the Consumer's search criteria. If no healthcare services and/or supplies are identified that meet the Consumer's search criteria, the System 1 presents alternative healthcare services and/or supplies that are available within the specified geographic search criteria. These alternative services and/or supplies are based on an analysis of the requested inputs using a medical knowledge base of the System 1, such that the alternative services and/or supplies attempt to solve the Consumers medical problem as reflected by the entered information.

The Consumer 2 selects one of the healthcare services or supplies listed by the System 1 to purchase. The Consumer 2 indicates they are a new or returning user of the System. The application programs of the System execute on the System hardware to provide the following features to the users of the system. The users access the system by using computers connected to the System servers through the internet. Primarily, this is done by providing web pages to the users on the user computers for displaying, and receiving, information.

Consumer Interactions:

These functions are provided primarily by the Consumer Subsystem operating in conjunction with the Web Server and Storage Subsystem.

New users of the System 1 are prompted to provide personal and billing information, including: first and last name, address, city, state, postal code, phone number, country of residence, email address, new password entry and confirmation of new password entry, credit card type, credit card number, credit card expiration date and credit card security code. Return users are prompted to provide their system identification name and password. Return users are prompted to provide billing information, including: credit card type, credit card number, credit card expiration date and credit card security code. The System prompts the user to view System 'Terms and Conditions' and 'Privacy Policy'. The user indicates agreement to the 'Terms and Conditions' and the 'Privacy Policy'. The System then allows the user to view the current order and correct the order or to proceed to confirm and submit the order.

The System presents the name of the healthcare services and/or supplies that have been identified, the corresponding CPT (Current Procedural Terminology) or HCPCS (Healthcare Common Procedure Coding System) code for the service or supply (where available), the price of the healthcare service and/or supply, the number of healthcare services/and or supplies available, the location of the healthcare service/and or supply, aggregate customer satisfaction survey scoring for the Producer (when available) and a brief description of the healthcare service/and or supply.

The System presents the user with the option to purchase a Transaction Guarantee. The user chooses to purchase the Transaction Guarantee or to decline the Transaction Guarantee.

The System presents the user with a summary of the completed order. Data elements presented include a unique order identification number, the name of the purchased healthcare service and/or supply, the corresponding CPT (Current Procedural Terminology) or HCPCS (Healthcare Common Procedure Coding System) code for the purchased service or supply (where available), the price of the healthcare service and/or supply, shipping fee, applicable taxes, applicable discounts, the location of the healthcare service/and or supply, customer satisfaction survey scoring for the Producer (when available), a brief prose description of the healthcare service/and or supply, and the shipping address of the Consumer where applicable.

The System presents the user with the name of the purchased healthcare service and/or supply, the corresponding CPT (Current Procedural Terminology) or HCPCS (Healthcare Common Procedure Coding System) code for the purchased service and/or supply (where available), the price of the healthcare service and/or supply, shipping fee, applicable taxes, applicable discounts, the location of the healthcare service/and or supply, customer satisfaction survey scoring for the Producer (when available), a brief description of the healthcare service/and or supply and the shipping address of the Consumer where applicable. The system prompts the Consumer to provide applicable gift card or coupon information.

In more detail, the system is used by the health-care Consumer as follows:

Consumer determines that the Consumer needs a healthcare service or supply. This may occur in a variety of circumstances; for example: the Consumer may be advised that he or she needs a healthcare service or supply by a healthcare provider; the Consumer may determine that he or she needs a healthcare supply or service based on symptoms they are experiencing; the Consumer may identify a healthcare service or supply that they need based on internet research. The Consumer accesses the System and searches for the healthcare service and or supply.

Consumers and HCS/S Producers discuss Consumers' HCS/S needs through the live "chat" function, and through these discussions, Consumers are provided with suggested names and/or corresponding CPT (Current Procedural Terminology) or HCPCS (Healthcare Common Procedure Coding System) codes for Consumer's specific HCS/S needs.

Also through the System live HCS/S provider 'chat' function and using the comprehensive HCS/S reference database, Consumers identify HCS/S that match their needs. They search the system by entering the name and/or corresponding CPT (Current Procedural Terminology) or HCPCS (Healthcare Common Procedure Coding System) codes for the HCS/S of interest, the time period they wish to obtain the HCS/S of interest, and geographic information (zip code) identifying where they would like to obtain the HCS/S of interest. Consumers may search the system with or without entering a CPT or HCPCS code.

The System provides availability and pricing information for the HCS/S matching the Consumer search criteria to the Consumer, all through the user GUI, over the Internet, using a user computer. Where no HCS/S matching the Consumer search criteria are available, alternative HCS/S matching the Consumer's geographic information (zip code) are presented when available.

The Consumer then selects and purchases (using the Consumer GUI) a health care supply or service. HCS/S purchased through the set price option are purchased for the listed HCS/S price. HCS/S purchased through the Auction process are purchased for the Final Sale Price.

The Consumer purchases the healthcare supply or service, such as by entering credit card information through a secure credit card payment system. The system, or a Producer, will process the payments in one of any number of known, or novel, ways. Other means of payment may also be available, such as through a payments service like PayPal, by debiting a checking account, etc.

The System presents the Consumer with a receipt for the completed sales transaction. Receipts are permanently stored in the System and may be retrieved by the Consumer at any time following the sales transaction. The transaction receipt includes the following information: name of item purchased, scheduled date and time of service (for services), order number, order total cost, order shipping cost, order tax, order status, order date and time, Producer name, Producer address, Producer telephone number and Producer email address.

For healthcare service purchases, the Consumer travels to the healthcare service Producer and receives the service from the Producer. For healthcare supply purchases, the Producer ships the supply to the Consumer, or the Consumer travels to the Producer and picks up the supply. The Consumer presents the receipt to the Producer and receives the service or supply in exchange for the receipt. No additional payment or personal information is required by the Producer in exchange for providing the healthcare service or supply.

The Consumer and Producer indicate to the System that the healthcare service or supply has been provided to the Consumer. The System then requests completion of a customer satisfaction survey from the Consumer, and Producer payment is credited to the Producer's System account.

The Consumer completes the customer satisfaction survey on the System (see below). The system issues payment for survey completion to the Consumer upon completion of the customer satisfaction survey. Consumer payment is made through a secure electronic transmission.

The System stores and compiles customer satisfaction survey data. These data are used to calculate and assign Producer Quality Scores. These quality scores are displayed alongside subsequent Producer product offerings. Quality scores are incorporated into Producer payment strategies. Producers are ranked according to quality scores into three tiers: Highest quality (Platinum Producers), top quartile Producers (Gold Producers), second quartile Producers (Silver Producers) and third quartile Producers (Bronze Producers). Producers with high quality scores receive increased reimbursement for subsequent sales.

Quality Survey Process

These functions are provided primarily by the Consumer Subsystem operating in conjunction with the Web Server and Storage Subsystem. The analysis functions can be provided by the Producer Subsystem, or a dedicated subsystem not shown.

Consumers enter customer satisfaction data after they obtain the purchased healthcare service and/or supply. The Consumer logs into the System by entering their customer identification name and password. The Consumer selects the 'My Past Orders' option.

The System presents a list of the Consumer's past orders. This list comprises all healthcare services and/or supplies that the Consumer has purchased through the System. The Consumer is presented with the option of viewing each past order. The Consumer selects a past order to review. The Consumer is presented with the option of printing the receipt for each past order. The Consumer is presented with the option of confirming that the purchased healthcare service and/or supply has been received. Where the Consumer confirms that the purchased healthcare service or supply has been received, the System presents the Consumer with the option of completing a customer satisfaction survey for the healthcare service and/or supply.

Where the Consumer elects to complete a customer satisfaction survey, the Consumer is presented with a multiple question customer satisfaction survey which includes a minimum of five Likert scale questions as well as the option to enter free text commentary on the quality of the healthcare service and/or supply. Where the Consumer provides the answer to all customer satisfaction survey questions, the Consumer is provided with an instant payment to their original credit card purchase account for a specified amount of money.

Producer Quality Analysis

Following receipt of the purchased HCS/S, the HCS/S Consumer is offered the option of completing a quality survey for the purchased HCS/S. For example, in the example embodiment, the Consumer is presented with the following five questions and assigns a score of 1, 2, 3 or 5 (Likert Scale) for each of the five questions:

I. I received the purchased healthcare service or supply from the provider
II. All of my questions regarding the healthcare service or supply were answered by the healthcare provider.
III. I would recommend this healthcare provider to my friends or family.
IIII. I would recommend The Company to my friends or family.
V. I received excellent customer service from this healthcare provider.

The Likert Scale used for this example embodiment is shown below:
1. Strongly disagree
2. Disagree
3. Neither agree nor disagree
4. Agree
5. Strongly agree In addition, the Consumer is able to enter a free text quality assessment of the HCS/S received.

For example, a HCS/S consumer receives a continuous positive airway pressure (CPAP) machine from a HCS/S producer. Following receipt of the machine, the Consumer scores the product as follows: I. 5; II. 5; III. 3; IIII. 3; V. 2.

In addition, the Consumer enters the following free text quality assessment of the CPAP machine:

I received the machine via regular mail service on the date of delivery promised by the provider. The machine words very well and is precisely the device that they described through the web browser. The customer service people who handled my telephone questions about the delivery date were not very helpful.'

The system generates a quality score of $(5+5+3+3+2)/5=3.6$ for the transaction and stores this score, along with the free text quality assessment, in association with this transaction. This score can then be utilized to provide a rating for the Producer for Consumers to compare producers to each other.

Producer Interactions

These functions are provided primarily by the Producer Subsystem operating in conjunction with the Web Server and Storage Subsystem.

Producers interact with the system in a manner similar to Consumers, i.e., via a web interface using a computer connected to the System via the Internet, but Producer interaction is quite different, as the user intends to use the system to sell goods and/or services.

Healthcare service and supply Producer System users of the System include physicians, nurse practitioners, physician's assistants, group practices, hospitals, durable medical equipment companies, independent laboratories, radiology companies and other entities. There are four product categories provided in the example embodiment: laboratory tests, radiology tests, physician services and medical supplies. Of course, additional categories could be accommodated, and some implementers might want to leave out some of the listed categories.

Producers list HCS/S available for purchase on the System. The Producer describes each service or supply offered for sale as outlined in the Producer information input section. Consumers search the site for health care supplies/and or services (described elsewhere in this disclosure).

Upon completion of a sales transaction, the System presents the Producer with a receipt for the completed sales transaction. Receipts are stored in the System and may be retrieved by the Producer at any time following the sales transaction.

For healthcare service purchases, the Producer provides the service to the Consumer at the scheduled time and place specified in the sales receipt. For healthcare supply purchases, the Producer ships the supply to the Consumer, or the Consumer travels to the Producer and picks up the supply. The Consumer presents the receipt to the Producer and receives the service or supply in exchange for the receipt. No additional payment or personal information is required by the Producer in exchange for providing the healthcare service or supply.

The Producer indicates on the System that the healthcare service or supply has been provided to the Consumer. The System then credits the Producer account for the sale price of the health care service or supply.

Producer Data Entry & Usage:

The Producer indicates they are a new or returning System user. Return users are prompted to provide their system identification name and password.

New users who are Producers are prompted to provide company name, company representative name, company role, address, state/province, country, postal code, specification of health product or service Producer status, email address, phone number, fax, preferred method of contact and new password selection. New user information is presented to the company for review. Producers meeting approval for participation are notified of their status as approved system Producers. Return users are prompted to provide their system identification name and password.

The Producer is presented with five information tabs: account information, account balance information, supplies/services listing, orders listing and create new order.

The account information tab lists the company name, company representative name, company representative role, address, state/province, country, postal code, specification of health product or service Producer status, email address, phone number, fax number and preferred method of contact. The user is presented with the option of entering a new password into the system.

The account balance tab presents the Producer's account transaction history. For each completed HCS/S sale, the account balance tab presents the date of the transaction, the time of the transaction, the currency amount credited to the Producer for the transaction and the order number for the transaction. The account balance tab presents each account withdrawal made by the Producer, including the date, time and amount of the withdrawal. The account balance tab presents the Producer with the total amount of money available to the Producer based on completed sales. The Producer is presented with the option of requesting a withdrawal from the account. Where the Producer elects to withdraw money from their account, the Producer designates the amount of money requested. This amount is then transferred to the Producer through a separate system.

The supplies/service tab presents the product title, date offered, price, number available, number sold, total revenue and activation status for each HCS/S listing. The system presents the Producer with the option of activating or deactivating each product. This tab presents the total amount of money earned through the system as of the current date. The Producer is presented with the option to review the data elements for each product listing. Activated products may not be edited. Products that are not activated may be edited.

The orders listing tab presents a list of orders. This list comprises all HCS/S that the Producer has offered for sale through the system. Each order includes these data elements: order date, order time, order number, order status and order price. The 'create new order' tab presents the Producer with the option to enter new products into the system.

The Producer enters descriptive information for HCS/S offerings. For each service offered, the Producer designates one of three service categories: radiology services, physician services or laboratory services. The Producer describes the service offering by selecting a service name and associated CPT (Current Procedural Terminology) or HCPCS (Healthcare Common Procedure Coding System) code(s) (where applicable), the date, time, frequency and quantity of services offered, a free text service description and the proposed offering price.

For healthcare services listed for sale through the auction system, the Producers designate the Auction Time Span, Minimum Bid and Purchase Now Price of the service.

For supply offerings, the Producer designates the supply offering by selecting a supply name and associated CPT (Current Procedural Terminology) or HCPCS (Healthcare Common Procedure Coding System) code(s) (where applicable), the date range and quantity of services offered, a free text supply description and the proposed offering price.

For healthcare supplies listed for sale through the auction system, the Producers designate the Auction Time Span, Minimum Bid and Purchase Now Price of the supply.

The Producer also indicates whether or not local pick up is required for the supply.

The Producer is presented with the option to review the data entered for the supply or service and editing the data elements.

The Producer is presented with the option of adding the supply or service to the account.

Where the Producer elects to add the supply or service to the account, the information is posted to the supplies/services listing tab.

The System assigns a unique Service/Supply Identification number to each new service and supply.

Producer Identification of Excess/Latent Unallocated Healthcare Services

Healthcare services are comprised of specific services provided at specific times in specific places. Producers identify healthcare services that have a low probability of sale through traditional (non out-of-pocket) purchase methods by monitoring the time period spanning: the current time and the time of the offered healthcare service. The time period spanning: the current time and the time of the offered healthcare service is inversely correlated with the probably that a healthcare service will be purchased. Producers list excess/unallocated healthcare services for sale through the System. Producers may modify elements of the offered service in order to attract Consumers to purchase excess/unallocated healthcare services.

Producers continuously review inventory to identify healthcare supplies that have a low probably of sale through traditional (non out-of-pocket) purchase methods. Producers also identify market prices for excess/unallocated healthcare services and supplies through the comprehensive HCS/S pricing database.

Producers can search the System by entering the name and/or corresponding CPT (Current Procedural Terminology) or HCPCS (Healthcare Common Procedure Coding System) codes for the healthcare services and/or supplies, the time period they wish to offer the healthcare services/and or supplies, and geographic information (zip code) identifying where they would like to offer the healthcare service and/or supplies. Producers cam then update HCS/S listing through the 'create new order' tab.

Producers need to identify the excess/unallocated healthcare services and supplies in order to use the System effectively. Examples of this process are provided in more detail later in this disclosure.

Payment & Money Flow

These functions can be distributed among the various subsystems based on the party primarily interacted with, or performed by a dedicated subsystem, not shown.

Figure 5:
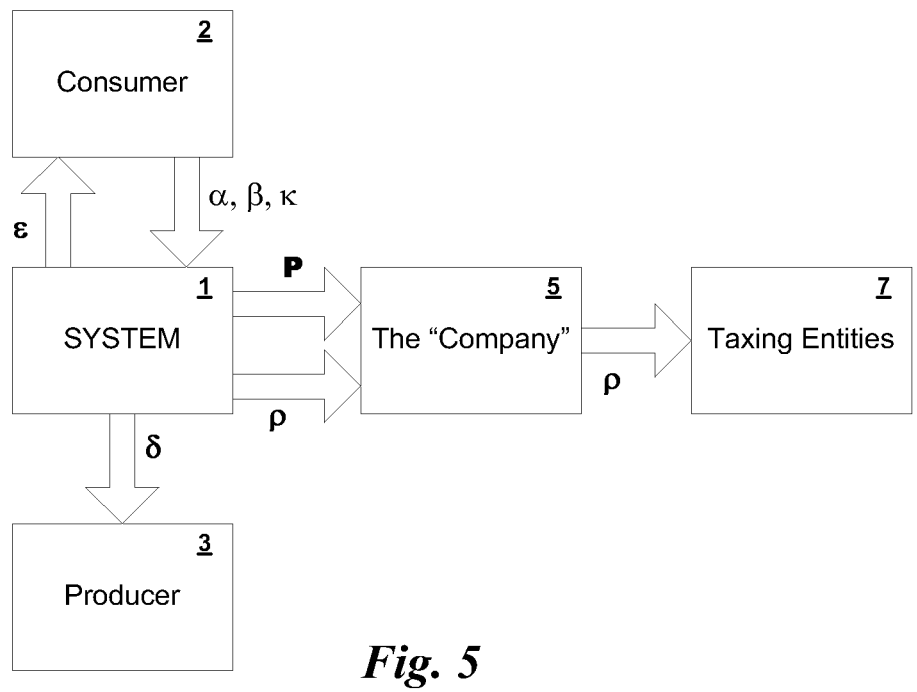
FIG. 5 shows a transaction flow for the example embodiment.

Producer payment rates are calculated based, in part, on Producer Quality Score rankings FIG. 5 shows a possible flow of money (or at least how the money is accounted for) between the entities using the example System. The System 1 collects full payment $\alpha$ from the Consumer 2 including any applicable sales taxes $\beta$ for the Healthcare Service or Supply from the Consumer at Point of Sale. Applicable taxes $\rho$ are then reserved for payment to the applicable taxing entity 7. The Consumer 2 is offered the option of purchasing $\alpha$ Transaction Guarantee $\kappa$ to reduce the risk of the transaction. Note that payment processors are not shown in the diagram, but may be a part of this money flow as well.

The System ultimately pays the Producer 3 a portion $\delta$ of the payment collected for the healthcare service or supply. Following Point of Service, the Consumer 2 is offered a transaction rebate $\epsilon$ in exchange for completion of a Consumer Satisfaction Survey. The remaining profit or loss P is credited/debited to the Company 5 operating/owning/maintaining the System 1. Table 10 shows these variables, and the equations showing only a few of many possible different scenarios are provided below:

Transaction equation; Transaction Guarantee not purchased This calculation is shown by Eq. 1:

$$P=\alpha+\beta-\rho-\delta-\epsilon \qquad \text{Eq. 1}$$

Transaction equation; Transaction Guarantee purchased; low Consumer satisfaction his calculation is shown by Eq. 2:

$$P=\alpha+\beta+\kappa-\rho-\delta-\epsilon-\alpha \qquad \text{Eq. 2}$$

Transaction equation; Transaction Guarantee purchased; high Consumer satisfaction: this calculation is shown by Eq. 3

$$P=\alpha+\beta+\kappa-\rho-\delta-\epsilon$$

TABLE 10

Transaction Variables

| Item | Description | System Credit or Debit |
|---|---|---|
| $\alpha$ | Service sale price | Credit |
| $\beta$ | Local Sales Tax | Credit |

TABLE 10-continued

Transaction Variables

| Item | Description | System Credit or Debit |
|---|---|---|
| ρ | Sales Tax Payment | Debit |
| κ | Transaction Guarantee | Credit |
| δ | Point of Service Producer payment | Debit |
| ε | Transaction rebate | Debit |
| P | Profit or loss | Transaction dependent |

Demographic Information

The "Company" reviews Consumer and Producer demographic information collected by the respective subsystems (in conjunction with the web server and storage subsystems). Demographic information may be updated, modified and/or corrected at the Company's discretion. Producer accounts are activated and deactivated at the Company's discretion.

The Company reviews HCS/S product information. Products may be reviewed, modified, activated or deactivated from sales queues at the Company's discretion.

The Company maintains a Producer HCS/S sales accounting system. This system includes a dataset for each pending and completed sales transaction. Data elements for each listing include the HCS/S unique identification number, service type, service or supply name, associated HCPCS/CPT code(s) where applicable, Auction or Set price designator, Listing Price, Sale Price, Payment to Producer. The accounting system provides real time summaries of Producer sales. Through this system, Producers are able to request and received direct deposit transfer of funds collected for completed sales transactions.

Consumer credit card numbers and Producer deposit bank account numbers are preferably not maintained in the System. Consumer credit card numbers and transactions are processed through a secure third party payment collection system. Producer deposit bank account information is maintained in a separate database.

The Company maintains a record of payments collected for each healthcare service and/or supply sale, payments made to Producers and payments made to Consumers for completion of quality survey.

The System preferably does not collect or store health information to avoid the liability and government regulations that such data can impose on the System.

The Flow of Goods (Supplies) and Services through the System

Examples

Goods and Services do not actually flow through the System. Goods and services are instead transacted through the System, and actually flow from Producers to Consumers outside of the System. The System itself facilitates this transaction.

Example Goods Flow:

Consumer Billy Jones selects and purchases a continuous positive airway pressure (CPAP) machine from 'Smith High Blood Pressure Clinic' through the System as outlined in Section 7.

Consumer Jones downloads the receipt for the purchased continuous positive airway pressure (CPAP) machine on the System and contacts the 'Smith High Blood Pressure Clinic' to determine a pick-up time for this supply. Consumer Jones picks up the supply.

Example Services Flow:

Consumer Jim Murdock selects and purchases a 'High Blood Pressure Treatments Services with Dr. Smith' service from 'Smith High Blood Pressure Clinic' through the System (this example is provided in more detail below).

Consumer Murdock downloads the receipt for the purchased 'High Blood Pressure Treatments Services with Dr. Smith' service on the System. Mr. Murdock goes to the address of the 'Smith High Blood Pressure Clinic' and receives the purchased 'High Blood Pressure Treatments Services with Dr. Smith' service at the time and date specified for this service.

Specific Case Example

Health Care Consumers

Starting the Process:

The Consumer, Mr. Murdock, uses his personal computer to access the website of the System via the Internet. He chooses the option to search the System, via the website, for high blood pressure treatment services. Thereby the Consumer searches the comprehensive HCS/S reference database and obtains the CPT code and service description information corresponding to high blood pressure treatment services. Using this information, Mr. Murdock (using the system) searches the healthcare service section for available high blood pressure treatment services. Mr. Murdock enters a free text description of high blood pressure treatment services into the consumer service search function or enters a primary care CPT code. Mr. Murdock indicates that he is seeking these services within a 50 mile radius of zip code 44889. Mr. Murdock indicates that he desires to receive this service on Jan. 17, 2011 and that he prefers to receive the service within seven days of Jan. 17, 2011.

The System identifies a high blood pressure treatment service provider within 50 miles of zip code 44889 offering the service on Jan. 20, 2011 from information that was entered by various Producers using the system. The system presents the price of this healthcare service of $201.25, the available time of 3:00 PM Eastern Standard time on Jan. 20, 2011, the CPT code for the office visit (99205), the average customer service satisfaction score of the provider of 4.75 out of a possible 5, and the following brief description of the service: 'Dr. Smith has 25 years experience treating hypertension. He has successfully treated the high blood pressure of 87% of his patients. His treatment strategies include a combination of lifestyle modification recommendations, western medicine treatment with medications and use of non-traditional treatments including acupuncture and meditation therapy. This visit will include a comprehensive review of your medical history, a complete physical examination, all blood work and testing required for evaluation of high blood pressure, a personalize high blood pressure treatment plan provided in both written form and through a confidential email reminder system and three follow up visits to monitor effectiveness of the high blood pressure treatment.' This information is provided to Mr. Murdock via a webpage served by the System to Mr. Murdock's computer.

Mr. Murdock selects this healthcare service for purchase. He indicates that he is a new System user. He is prompted by the System to provide the information of Table 11 via the website using his computer:

TABLE 11

Example Consumer Procedure

| | |
|---|---|
| Name: | Jim Murdock |
| Address: | 314 Railroad Avenue; Wakeman, Ohio; 44889 |
| Phone Number: | 440-774-5566 |
| Country of Residents: | United States of America |
| Email Address/Customer ID: | Jmurdo@graingrowers.org |
| New Password Entry: | Ireland01 |
| Password Confirmation: | Ireland01 |
| Credit Card Type: | MasterCard |
| Credit Card Number: | 9998345612344576 |
| Credit Card Expiration Date: | Jan. 15, 2016 |
| Credit Card Security Code: | 543 |

The System prompts Mr. Murdock to view System 'Terms and Conditions' and 'Privacy Policy' and other legal information, if relevant. Mr. Murdock indicates his agreement to the 'Terms and Conditions' and the 'Privacy Policy', such as by mouse click on an "accepted" button.

The System the permits Mr. Murdock to view the order for 'High Blood Pressure Treatment Services with Dr. Smith' and prompts Mr. Murdock to correct the order, if necessary. The System allows Mr. Murdock to make corrections, if necessary, via the website. He reviews the order and notes that no corrections are necessary. He confirms the order and submits the order via the System website.

The System provides Mr. Murdock with the option to purchase a Transaction Guarantee. Mr. Murdock elects to decline the Transaction Guarantee option.

The System presents Mr. Murdock with the information shown in table 12 as a confirmation:

TABLE 12

Example Consumer Procedure (cont'd)

| | |
|---|---|
| Name of the purchased healthcare service and/or supply: | High Blood Pressure Treatment Services with Dr. Smith |
| CPT (Current Procedural Terminology) code for the office visit: | 99205 |
| Price of the healthcare service and/or supply: | $201.25 |
| shipping fee: | Not applicable |
| Applicable taxes | 2% (State of Ohio) = $ 4.02 |
| Applicable discounts: | None |
| Location of the healthcare service/and or supply: | Smith High Blood Pressure Clinic; 1650 Lorain Avenue; Lorain, Ohio 44889 |
| Date and Time of Appointment: | 3:00 PM Eastern Standard time on Jan. 20th, 2011 |
| Average customer satisfaction survey score: | 4.75 out of 5 |
| The shipping address of the Consumer: | Not applicable |

The system also provides Mr. Murdock with the following Description of the healthcare service/and or supply:

Dr. Smith has 25 years experience treating hypertension. He has successfully treated the high blood pressure of 87% of his patients. His treatment strategies include a combination of lifestyle modification recommendations, western medicine treatment with medications and use of non-traditional treatments including acupuncture and meditation therapy. This visit will include a comprehensive review of your medical history, a complete physical examination, all blood work and testing required for evaluation of high blood pressure, a personalize high blood pressure treatment plan provided in both written form and through a confidential email reminder system and three follow up visits to monitor effectiveness of the high blood pressure treatment.

The system prompts Mr. Murdock to provide applicable gift card or coupon information, and Mr. Murdock submits the order.

The System presents a summary of the completed order to Mr. Murdock, which can show much or all of the data of Table BBB, along with a unique order identification number for reference purposes. Mr. Murdock can print this information, if desired, and it can be provided to him by the System on subsequent visits to the website by his logging into his account.

Receiving the Treatment:

Mr. Murdock goes to Dr. Smith for his appointment at 3:00 PM Eastern Standard time on Jan. 20, 2011, where he receives his chosen medical service from the chosen provider, Dr. Smith. Because he has already paid for the service, no payment need be provided at the time of treatment.

Followup:

Following the appointment, Mr. Murdock logs onto the System by using his computer accessing the System Website by entering his email Address/Customer ID jmurdo@graingrowers.org and password: Ireland01. Mr. Murdock selects the 'My Past Orders' option.

The System presents a list of Mr. Murdock's past orders. This list comprises all healthcare services and/or supplies that Mr. Murdock has purchased through the System. Because the high blood pressure visit was Mr. Murdock's first purchase through the system, this is the only past order available for review by him. Mr. Murdock selects his 'High Blood Pressure Treatment Services with Dr. Smith' order for review. Mr. Murdock is presented with the option of printing the receipt for this order. He declines, but he can print this receipt at a later time, if desired. Mr. Murdock is presented with the option of confirming that he has received the purchased "High Blood Pressure Treatment Services with Dr. Smith". Mr. Murdock confirms that he has received the 'High Blood Pressure Treatment Services with Dr. Smith'.

Satisfaction Survey:

In response to the confirmation that the service has been received, the System presents Mr. Murdock with the option of completing a customer satisfaction survey for the 'High Blood Pressure Treatment Services with Dr. Smith'. Incentives may be offered to Mr. Murdock in order to encourage him to complete the survey.

Mr. Murdock elects to complete the customer satisfaction survey. He is presented by the system (via the website) with a multiple question customer satisfaction survey which includes the following five Likert scale questions for the 'High Blood Pressure Treatment Services with Dr. Smith' service:

I. I received the purchased healthcare service or supply from the provider.
    II. All of my questions regarding the healthcare service or supply were answered by the healthcare provider.
    III. I would recommend this healthcare provider to my friends or family.
    IIII. I would recommend The Company to my friends or family.
    V. I received excellent customer service from this healthcare provider.

Mr. Murdock is given the following options for answering each of these questions:

1. Strongly disagree
2. Disagree
3. Neither agree nor disagree
4. Agree
5. Strongly agree Mr. Murdock assigns the following scores to the questions: I. 4; II. 3; III. 5; IIII. 1; and V. 5.

Mr. Murdock enters the following free text commentary for the 'High Blood Pressure Treatment Services with Dr. Smith' service in a field provided by the System for such comments:

Dr. Smith was courteous and knowledgeable. He answered most of my questions about my high blood pressure. He sent me for lab tests, provided a prescription for a new medication and scheduled two follow up visits to check my progress. I recommend the 'High Blood Pressure Treatment Services with Dr. Smith' service very highly.'

Mr. Murdock's credit card account is paid $10 for completion of the customer satisfaction survey when his survey questions are entered into the system as a reward for having completed the survey. The survey information provided by Mr. Murdock is used by the system to update the quality review information of Dr. Smith for providing to Consumers.

Mr. Murdock can access the system in the future to retrieve information about this procedure, and to search for other medical products and/or services that he may need, as desired. Thus, the System can become a resource for the consumer to monitor his medical treatments obtained through the system.

Specific Example Cont'd

Health Care Producers

Dr. Smith's administrative assistant accesses the System website using an office computer. The assistant indicates that Dr. Smith's medical practice is a returning System user. She enters system identification name 'smith@smithcare.com' and password 'health' into the system to access their account. Dr. Smith's medical practice has previously entered all demographic information into the System. This information has been reviewed by the Company and Dr. Smith's medical practice has been approved as a System Producer. The assistant interacts with the System in the following manner via the System website over the Internet using the office computer:

Dr. Smith's assistant is presented with five information tabs: account information, account balance information, supplies/services listing, orders listing and create new order. The account information tab includes the information shown in Table 13:

TABLE 13

Example Producer Procedure

| | |
|---|---|
| Company Name: | Smith High Blood Pressure Clinic |
| Company representative name: | Susan Jones |
| Company representative role: | Administrative Assistant |
| Company Address: | 1650 Lorain Avenue; |
| City: | Lorain |
| State/province: | Ohio |
| Country: | USA |
| Postal code: | 44889 |
| Specification of health product or service Producer status: | Approved |
| Email address: | smith@smithcare.com |
| Phone number: | 440-889-7634 |
| Fax number | 440-839-2967 |
| Preferred method of contact: | email |

Dr. Smith's administrative assistant is presented with the option of entering a new password into the system. She declines.

The account balance tab presents the Smith High Blood Pressure Clinic's account transaction history.

For the healthcare service sold to Mr. Murdock, the account balance tab presents the information shown in TABLE 14:

TABLE 14

Example Producer Procedure (cont'd)

| | |
|---|---|
| The date of the transaction: | Jan. 18th, 2011 |
| The time of the transaction: | 6:00 AM Eastern Standard time |
| The currency amount credited to the Smith High Blood Pressure Clinic for the transaction: | $181.12 |
| The order number for the transaction: | 34561235 |

The account balance tab presents Dr. Smith's administrative assistant with the total amount of money available to the Producer based on completed sales. There is one completed sale, and the total amount of money available to the Smith High Blood Pressure Clinic is $180.02.

Dr. Smith's administrative assistant is presented with the option of requesting a withdrawal from the account. Dr. Smith's administrative assistant elects to withdraw $100 from the Smith High Blood Pressure Clinic account. $100 deposit is made to the Smith High Blood Pressure Clinic deposit account on record with The Company (representing/operating/owning the System) at the close of business on the first business day following the day of the request.

The supplies/services tab presents the information for this completed transaction shown in TABLE 15:

TABLE 15

Example Producer Procedure (cont'd)

| | |
|---|---|
| The product title: | High Blood Pressure Treatment Services with Dr. Smith |
| Date offered | Jan. 10th, 2011 |
| List price: | $201.25 |
| Number available: | 0 |
| Number sold: | 1 |
| Total revenue: | $180.02 |
| Activation status: | Activated |

The My Balance tab indicates a total of $180.02 earned through the system as of the close of the first business day following Jan. 20, 2011.

The product offerings listing tab presents a list of current product offerings. This list comprises all HCS/S that the Producer has offered for sale through the system. Each product offering listing includes these data elements: order date, order time, order number, order status and order price.

Dr. Smith's administrative assistant is presented with the option to review the data elements for each product offering. She reviews the current product offerings and chooses not to modify any of the data for the current product offerings.

Listing Producer Services:

Producer Identification of Excess/Unallocated Healthcare Services Hypothetical:

Dr. Smith's administrative assistant reviews the current service inventory of the Smith High Blood Pressure Clinic by reviewing the Smith High Blood Pressure Clinic internal appointment record system. Services that have a short time span between the time of her review and the scheduled time of service have a lower probability of sale through traditional (non out-of-pocket) purchase methods. As these service times of unsold service inventory approaches, she elects to list the services for sale through the System. Dr. Smith's administrative assistant identifies unsold Knee X-ray service inventory offered through traditional (non out-of-pocket) purchase methods scheduled for two business days in the future. She elects to list these services through the System through the Auction option. The following day, she notes that these services have not been sold through the system. She elects to re-list these X-ray services through the System at a discounted set price. Both services are purchased through this discounted set price, and the previously unsold service inventory is sold.

Producer Identification of Excess/Unallocated Healthcare Supplies Hypothetical:

Dr. Smith's administrative assistant reviews the current supply inventory of the Smith High Blood Pressure Clinic by reviewing the Smith High Blood Pressure Clinic internal inventory system. She notes that there are three Continuous Positive Airway Pressure (CPAP) Machine's in the current inventory that have not been sold over a six month period. She elects to list all three CPAP machines through the System Auction option. She provides data for the CPAP machines as listed previously. All three CPAP machines sell on the day of listing for a greater price than the initial listed Auction Price.

Market Research:

Dr. Smith's administrative assistant reviews the System comprehensive HCS/S pricing database for current market pricing of unsold supply and service inventory. She searches the system by entering the name and/or corresponding CPT (Current Procedural Terminology) or HCPCS (Healthcare Common Procedure Coding System) codes for unsold supply and service inventory, the time period they wish to offer the unsold supply and service inventory, and geographic information (zip code) identifying where they would like to offer the unsold supply and service inventory.

She notes that CPAP machines sell for higher prices in the Pacific Northwest in the months of September and October, and she decides to list additional unsold CPAP machine inventory for sale in the Pacific Northwest during that time period. She notes that Knee X-ray supplies are limited in Ohio, and she elects to list unsold knee X-ray service inventory through the Auction bidding process.

Dr. Smith's administrative assistant desires to enter three new offerings into the system. Dr. Smith's administrative assistant enters descriptive information for two new healthcare services and one new healthcare supply offering, as shown in tables 16 & 17.

TABLE 16

New Services Listing:

| | SERVICE 1 | SERVICE 2 |
|---|---|---|
| Service Type | Radiology Service | Laboratory Service |
| Service Name | Knee X-ray | Arthritis blood test for Gout |
| CPT or HCPCS Code | CPT 73560 | CPT 84550 |
| Date Available | Nov. 11th, 2010 | Oct. 1st, 2010 |
| Time Available | 08:00 AM | 10:15 AM |
| Frequency of Availability | Daily | Daily |
| Quantity Offered | 1 | 5 |
| Service Description | X-RAY EXAM OF KNEE, 1 OR 2 | URIC ACID; BLOOD |
| Proposed Offering Price | $40.00 | $10 |
| Auction or Set Price | Set | Auction |
| Auction Start Date | NA | Sep. 1st, 2010 |
| Auction Start Time (EST) | NA | 08:00 |
| Auction Time Span | NA | 5 days |
| Minimum Bid | NA | $10 |
| Purchase Now Price | NA | $20 |

TABLE 17

New Healthcare Supply Listing:

| | |
|---|---|
| Supply Name | Continuous Positive Airway Pressure (CPAP) Machine |
| CPT or HCPCS Code | E0601 |
| Availability Date Range | Aug. 15th - Nov. 15th, 2011 |
| Quantity of Supplies offered | 10 |
| Free text supply description | Basic Continuous Positive Airway Pressure (CPAP) Machine - reconditioned. Comes with one CPAP mask, tubing and a one month money back guarantee |
| Proposed offering price | $225 |
| Auction or Set Price | Set Price |
| Auction Time Span | NA |
| Minimum Bid | NA |
| Purchase Now Price | NA |
| Local pickup required? | no |

Dr. Smith's administrative assistant is presented with the option to review the data entered for these two new service offerings and one new supply offering. She reviews the data entry and confirms that the data entry is correct. Dr. Smith's administrative assistant is presented with the option of adding the new supply and services to the account. She adds both new services and the new supply to the account.

The two new services and one new supply are then posted under the supplies/services listing tab. The System assigns a unique Service/Supply Identification number to each new service and supply. Thus, these new services and supply are made available via the System to Consumers who may desire them, and the process repeats.

Producer HCS/S Listing Update Process:

Dr. Smith's administrative assistant continuously updates the Smith High Blood Pressure Clinic health care service and supply listings through the 'create new order' tab.

Additional Examples

Consumer and Producer System Use and the Flow of Money Through the System

Example

In this example, the System makes financial calculations based on a 2% sales tax, a Transaction Guarantee price of $10, a Consumer survey payment of $10 and a Producer Payment Rate of 90%. The System can apply any percentage or dollar amount to these variables.

Consumer 'Jim Murdock' identifies the service 'High Blood Pressure Treatments Services with Dr. Smith' on the System. The price of this service is $205.27 ($201.25 sale price+$4.02 for the 2% local sales tax).

'Jim Murdock' reviews the description of the service, including the time and date availability and location as well as prior quality scores for 'High Blood Pressure Treatments Services with Dr. Smith' and decides to purchase this service. Vim Murdock' purchases the service for $205.27. $4.02 is allocated for payment to the taxing entity. Consumer Vim Murdock' presents the transaction sales receipt for 'High Blood Pressure Treatments Services with Dr. Smith' to the 'Smith High Blood Pressure Clinic'.

Consumer Vim Murdock' is offered the option of purchasing a Transaction Guarantee for 'High Blood Pressure Treatments Services with Dr. Smith' for $10.00. He declines.

The 'Smith High Blood Pressure Clinic' provides the for 'High Blood Pressure Treatments Services with Dr. Smith' services to Consumer Vim Murdock'.

The 'Smith High Blood Pressure Clinic' and Consumer Vim Murdock' indicate that the 'Smith High Blood Pressure Clinic' has provided for 'High Blood Pressure Treatments Services with Dr. Smith' to Consumer 'Jim Murdock' by entering this information into their respective accounts in the System (please see Sections 1 and 2 for details of Consumer and Producer use of the System).

The System pays the Producer $180.02 for the Healthcare Service or Supply at Point of Service. The System offers Consumer Vim Murdock' $10.00 in exchange for completion of a for 'High Blood Pressure Treatments Services with Dr. Smith' Consumer satisfaction survey. Consumer 'Jim Murdock' completes the satisfaction survey, and the System credits Mr. Murdock's account $10.

There is a $21.23 profit to be retained by the Company. See Table 18 for a summary.

TABLE 18

Consumer and Producer System use and the flow of money through the System: Example

| Description | System Credit or Debit |
|---|---|
| Service sale price | +$201.25 |
| Local Sales Tax | +$4.02 |
| Sales Tax Payment | −$4.02 |
| Transaction Guarantee | 0 |
| Point of Service Producer payment | −$180.02 |
| Transaction rebate | 0 |
| Profit or loss | +$21.23 |

Example

Consumer and Producer System Use and the Flow of Money Through the System with Transaction Guarantee; Low Consumer Satisfaction In this example, the System makes financial calculations based on a 2% sales tax, a Transaction Guarantee price of $10, a Consumer survey payment of $10, a Producer Payment Rate of 90% and a $95^{th}$ percentile Satisfaction Threshold. The System can apply any percentage or dollar amount to these variables.

Consumer 'Jim Murdock' identifies the service 'High Blood Pressure Treatments Services with Dr. Smith' on the System. The price of this service is $205.27 ($201.25 sale price+$4.02 for the 2% local sales tax).

Vim Murdock' reviews the description of the service, including the time and date availability and location as well as prior quality scores for 'High Blood Pressure Treatments Services with Dr. Smith' and decides to purchase this service. Vim Murdock' purchases the service for $205.27. $4.02 is allocated for payment to the taxing entity. Consumer Vim Murdock' presents the transaction sales receipt for 'High Blood Pressure Treatments Services with Dr. Smith' to the 'Smith High Blood Pressure Clinic'.

Consumer 'Jim Murdock' is offered the option of purchasing a Transaction Guarantee for 'High Blood Pressure Treatments Services with Dr. Smith' for $10.00. He accepts the offer.

The 'Smith High Blood Pressure Clinic' provides the for 'High Blood Pressure Treatments Services with Dr. Smith' services to Consumer 'Jim Murdock'.

The 'Smith High Blood Pressure Clinic' and Consumer 'Jim Murdock' indicate that the 'Smith High Blood Pressure Clinic' has provided for 'High Blood Pressure Treatments Services with Dr. Smith' to Consumer 'Jim Murdock' by entering this information into their respective accounts in the System (details of Consumer and Producer use of the System are provided in earlier sections of this disclosure).

The System pays the Producer $180.02 for the Healthcare Service or Supply at Point of Service. The System offers Consumer Vim Murdock' $10.00 in exchange for completion of a for 'High Blood Pressure Treatments Services with Dr. Smith' Consumer satisfaction survey. Consumer Vim Murdock' completes the satisfaction survey, and the System credits Mr. Murdock's account $10.

'Mr. Murdock' completes the HCS/S satisfaction survey. His satisfaction is noted to be less that the $95^{th}$ percentile Satisfaction Threshold for all quality surveys in the System for purchases made with Transaction Guarantees. The System Credit's 'Mr. Murdock's' payment account for the full 'High Blood Pressure Treatments Services with Dr. Smith' purchase price of $205.27.

There is a $170.02 loss is retained by the "Company". Table 19 provides a Summary of this transaction:

TABLE 19

Summary: Consumer and Producer System use and the flow of money through the System with Transaction Guarantee; low Consumer satisfaction

| Item | Description | System Credit or Debit |
|---|---|---|
| A | Service sale price | +$201.25 |
| B | Local Sales Tax | +$4.02 |
| C | Sales Tax | −$4.02 |

TABLE 19-continued

Summary: Consumer and Producer System use
and the flow of money through the System with Transaction
Guarantee; low Consumer satisfaction

| Item | Description | System Credit or Debit |
|---|---|---|
| G | Payment Transaction Guarantee | +$10.00 |
| D | Point of Service Producer payment | −$180.02 |
| E | Transaction rebate | −$205.27 |
| F | Profit or loss | −$170.02 |

Example

Consumer and Producer System Use and the Flow of Money Through the System with Transaction Guarantee; High Consumer Satisfaction In this example, the System makes financial calculations based on a 2% sales tax, a Transaction Guarantee price of $10, a Consumer survey payment of $10, a Producer Payment Rate of 90% and a 95$^{th}$ percentile Satisfaction Threshold. The System can apply any percentage or dollar amount to these variables.

Consumer 'Jim Murdock' identifies the service 'High Blood Pressure Treatments Services with Dr. Smith' on the System. The price of this service is $205.27 ($201.25 sale price+$4.02 for the 2% local sales tax).

'Jim Murdock' reviews the description of the service, including the time and date availability and location as well as prior quality scores for 'High Blood Pressure Treatments Services with Dr. Smith' and decides to purchase this service. Vim Murdock' purchases the service for $205.27. $4.02 is allocated for payment to the taxing entity. Consumer Vim Murdock' presents the transaction sales receipt for 'High Blood Pressure Treatments Services with Dr. Smith' to the 'Smith High Blood Pressure Clinic'.

Consumer Vim Murdock' is offered the option of purchasing a Transaction Guarantee for 'High Blood Pressure Treatments Services with Dr. Smith' for $10.00. He accepts the offer. The 'Smith High Blood Pressure Clinic' provides the for 'High Blood Pressure Treatments Services with Dr. Smith' services to Consumer Vim Murdock'.

The 'Smith High Blood Pressure Clinic' and Consumer Vim Murdock' indicate that the 'Smith High Blood Pressure Clinic' has provided for 'High Blood Pressure Treatments Services with Dr. Smith' to Consumer 'Jim Murdock' by entering this information into their respective accounts in the System (see previous sections for details of Consumer and Producer use of the System).

The System pays the Producer $180.02 for the Healthcare Service or Supply at Point of Service. The System offers Consumer 'Jim Murdock' $10.00 in exchange for completion of a for 'High Blood Pressure Treatments Services with Dr. Smith' Consumer satisfaction survey. Consumer 'Jim Murdock' completes the satisfaction survey, and the System credits Mr. Murdock's account $10.

'Mr. Murdock' completes the HCS/S satisfaction survey. His satisfaction is noted to be greater than the 95$^{th}$ percentile Satisfaction Threshold for all quality surveys in the System for purchases made with Transaction Guarantees.

A $31.23 profit is retained by the Company. Table 20 provides a summary of this transaction

TABLE 20

Summary: Consumer and Producer System use
and the flow of money through the System with
Transaction Guarantee; high Consumer satisfaction

| Item | Description | System Credit or Debit |
|---|---|---|
| A | Service sale price | +$201.25 |
| B | Local Sales Tax | +$4.02 |
| C | Sales Tax Payment | −$4.02 |
| G | Transaction Guarantee | +$10.00 |
| D | Point of Service Producer payment | −$180.02 |
| E | Transaction rebate | 0 |
| F | Profit or loss | $31.23 |

Example

Auction Bidding System

Producer 'Smith High Blood Pressure Clinic' lists the service shown in Table 21 for sale through the Auction Bidding System:

TABLE 21

Auctionable Service Listing #1
Service

| Service Type | Laboratory Service |
|---|---|
| Service Name | Arthritis blood test for Gout |
| CPT or HCPCS Code | CPT 84550 |
| Date Available | Oct. 1$^{st}$, 2010 |
| Time Available | 10:15 AM |
| Frequency of Availability | Daily |
| Quantity Offered | 1 |
| Service Description | URIC ACID; BLOOD |
| Proposed Offering Price | $10 |
| Auction or Set Price | Auction |
| Auction Start Date | Sep. 1$^{st}$, 2010 |
| Auction Start Time (Eastern Standard Time) | 0:800 |
| Auction Time Span | 5 days |
| Minimum Bid | $10 |
| Purchase Now Price | $20 |

Two Consumers identify this Service through the System and Bid for the Service as shown in Table 22

TABLE 22

Auction #1 Bidding Timeline

| Date | Time | Consumer #1 Laboratory Service BID | Consumer #2 Laboratory BID | Minimum BID Price |
|---|---|---|---|---|
| Aug. 21, 2010 | | | | $10 |
| Sep. 1, 2010 | 08:15 | $12 | $14 | $14 |
| Sep. 1, 2010 | 12:15 | $15 | | $15 |
| Sep. 4, 2010 | 03:00 | | 18$ | $18 |
| Sep. 6, 2010 | 08:00 | | | |

On Sep. 6, 2010 at 08:00 EST, the listing expires. Consumer #2 purchases the Laboratory Service for the Final Sale Price of $18.

Producer 'Smith High Blood Pressure Clinic' lists a Supply for sale through the Auction Bidding System as shown in Table 23:

TABLE 23

Auctionable Service Listing #2
Supply

| | |
|---|---|
| Supply Name | Continuous Positive Airway Pressure (CPAP) Machine |
| CPT or HCPCS Code | E0601 |
| Availability Date Range | Aug. 15$^{th}$-Nov. 15$^{th}$, 2011 |
| Quantity of Supplies offered | 1 |
| Free text supply description | Basic Continuous Positive Airway Pressure (CPAP) Machine - reconditioned. Comes with one CPAP mask, tubing and a one month money back guarantee |
| Proposed offering price | $225 |
| Auction or Set Price | Auction |
| Auction Start Date | Nov. 2nd, 2010 |
| Auction Start Time (Eastern Standard Time) | 12:00 |
| Auction Time Span | 20 days |
| Minimum Bid | $225 |
| Purchase Now Price | $400 |
| Local pickup required? | no |

Four Consumers identify this Supply through the System and Bid for the Service as shown in Table 24:

TABLE 24

Auction #2 Bidding Timeline

| Date | Time | Consumer #1 | Consumer #2 | Consumer #3 | Consumer #4 | Minimum BID Price |
|---|---|---|---|---|---|---|
| Nov. 2, 2010 | | | | | | $225 |
| Nov. 5, 2010 | 08:15 | $225 | $227 | $298 | $412 | $412 |
| Nov. 7, 2010 | 12:15 | $413 | | | | $413 |
| Nov. 11, 2010 | 03:00 | | | | $416 | $416 |
| Nov. 22, 2010 | 12:00 | | | | | $416 |

On Nov. 22, 2010 @ 12:00 EST, the listing expires. Consumer #4 purchases the Supply for the Final Sale Price of $416.

Producer Data Modification Example:

The Company receives an email message from the Centers for Medicare and Medicaid Services questioning the validity of a product listing on the System. The Company reviews the System product listing and notes that the Producer's product description and HCPCS coding for the product listing at issue do not correspond to each other and could be confusing to a Consumer. The Company contacts the Producer and determines that the Producer has entered this information in error. The Producer requests that the Company delete the product listing immediately. The Company deletes the System product listing.

Consumer Data Analysis Example:

The Company is contacted by a Producer with unsold wheelchair inventory requesting assistance in selling this inventory. The Company reviews the System wheelchair Supply search history and notes a significant concentration of Consumer wheelchair Supply searches in Minnesota. The Company provides this information to the Producer. The Producer elects to list the unsold wheelchair inventory at deep discounts in Minnesota through the System. All inventory is sold.

Consumer and Producer Demographic Data Review Examples:

The Company is notified by a Consumer that a Producer's System address is incorrect. The Company contacts the Producer and confirms that the address is incorrect and confirms the correct address. The Company corrects the Producer's System Address.

The Company receives three Producer reviews with quality scores of 1 out of 5 on the same day for the same Producer. The Company emails the Producer at the Producer's listed preferred email address. The Company does not receive a reply to the email within two hours of the inquiry. The Company immediately deactivates the Producer account.

A Consumer contacts the Company and states that the Consumer has forgotten the Consumer's secure System Password. The Company confirms the Consumer's identity and permits the Consumer to remotely update the Consumer's System Password. The Company reviews the current product listings of the Smith High Blood Pressure Clinic and notes that the Smith High Blood Pressure Clinic has listed 40,000 CPAP machines for sale. The company de-activates the product listing and contacts the Smith High Blood Pressure Clinic. Dr. Smith's administrative assistant confirms that they had intended to list 40 CPAP machines for sale. The Company changes the Smith High Blood Pressure Clinic CPAP product listing to 40 CPAP machines and re-activates the product listing.

Producer Healthcare Service and Supply Sales Accounting System Example: Healthcare Service and Supply Sales Accounting Data: Smith High Blood Pressure Clinic Dr. Smith's administrative assistant reviews the following Smith High Blood Pressure Clinic healthcare service and supply sales accounting information, and she notes that three items have been sold through the System for a total available payment of $259.50. Table 25 shows a Record of payments collected for each healthcare service and/or supply sale, payments made to Producers and payments made to Consumers for completion of quality survey.

TABLE 25

Record of Payments

| | Pending or Completed | | | | |
|---|---|---|---|---|---|
| | Pending | Completed | Completed | Completed | Pending |
| HCS/S unique identification number | 5671454 | 5671455 | 5671456 | 5671457 | 5671458 |
| Service Type | Radiology | Radiology | Laboratory | NA | NA |
| Service Name | Knee X-ray | Knee X-ray | Knee X-ray | NA | NA |
| Supply Name | NA | NA | NA | CPAP Machine | CPAP Machine |
| HCPCS/CPT code(s) | 73650 | 73650 | 84550 | E0601 | E0601 |
| Auction or Set Price | Set | Set | Auction | Set | Set |
| Listing Price | $40 | $40 | $10 | $225 | $225 |

TABLE 25-continued

Record of Payments

| | Pending or Completed | | | |
|---|---|---|---|---|
| | Pending | Completed | Completed | Completed | Pending |
| Sale Price | $40 | $40 | $15 | $225 | $225 |
| Payment to Producer | $36 | $36 | $13.50 | $210 | $210 |
| Quality Survey Consumer Payment | NA | $5 | 0$ | $10 | NA |

Doctor Smith requests a direct deposit of $200 to the Smith High Blood Pressure Clinic checking account number on file with the "Company". The "Company" deposits $200 into the Smith High Blood Pressure Clinic before the close of business on the next business day.

Producer deposit bank account information is maintained in a database that is not accessible to or contained within the System.

The invention has been described hereinabove using specific examples and embodiments; however, it will be understood by those skilled in the art that various alternatives may be used and equivalents may be substituted for elements and/or steps described herein, without deviating from the scope of the invention. Modifications may be necessary to adapt the invention to a particular situation or to particular needs without departing from the scope of the invention. It is intended that the invention not be limited to the particular implementations and embodiments described herein, but that the claims be given their broadest reasonable interpretation to cover all embodiments, literal or equivalent, disclosed or not, covered thereby.

What is claimed is:

1. A method for using a computerized system for matching healthcare consumers to healthcare producers comprising the steps of:
    providing a producer interface to the system for each of a plurality of healthcare producers to interact with the system over the Internet;
    providing a consumer interface to the system for each of a plurality of healthcare consumers to interact with the system over the internet, wherein said consumer interface presents a standardized quality assessment of each one of the producers;
    accepting, via the producer interface, one or more available products and/or available services listings from each of a plurality of healthcare producers;
    accepting, via the consumer interface, a request from one consumer who is one of said plurality of consumers regarding a desired healthcare product or service;
    searching, using the system, the plurality of products and/or services listed by the plurality of producers for a subset of said products and/or services that are a close match to the requested desired healthcare product or service;
    providing a list of one or more items of said subset of products and/or services for display to the one consumer;
    offering said items on said list of items for purchase by the one consumer;
    for any one or more items of said offered items accepted for purchase by the one consumer, performing the steps of:
        accepting payment information regarding the accepted purchase(s) by the one consumer for the one or more items purchased,
        allocating a portion of said payment(s) to the producer(s) corresponding to the purchased item(s),
        requesting and receiving, from the one consumer, quality information about each one of the one or more purchased items, and
        allocating a remaining portion of said payment, if any, to a representative of the system; and
    using said quality information provided by the one consumer for calculating an updated standardized quality assessment for the producer(s) of the one or more purchased items.

2. The method of claim 1, further comprising the step of offering a transaction guarantee to the one consumer for purchase, wherein if the one consumer purchases said transaction guarantee and said quality assessment provides a determination that one or more of the one or more product(s) and/or service(s) purchased by the one consumer did not meet a quality threshold, at least a partial refund is provided to the one consumer.

3. The method of claim 2, wherein said at least partial refund is at least partially deducted from the portion of said payment provided to the corresponding producer(s).

4. The method of any of claim 1, wherein said step of offering said items on said list of items for purchase by the one consumer is accomplished via an auction process provided by the system, and wherein the one consumer is only offered the items for purchase if the one consumer wins the auction.

5. The method of any of claim 1, wherein said system accepts full payment for the purchased items from the one consumer prior to the corresponding producer(s) actually delivering the product(s) and/or performing the service(s) that were purchased by the one consumer.

6. The method of claim 5, wherein said portion of the payment allocated to the corresponding producer(s) is provided after said product or service has been provided by the corresponding producer(s).

7. The method of claim 5, wherein said payment is processed by a third-party payment processor.

8. The method of claim 1, wherein payment for the purchase from the one consumer and the allocated payments are processed by a third-party payment processor.

9. The method of claim 1, wherein a comprehensive HCS/S reference database is utilized during said searching step, wherein said database includes a plurality of the items from the list of items consisting of: symptoms associated with common medical conditions; operating characteristics and descriptions of common medical screening tests; Current Procedural Terminology (CPT) code definitions, and Healthcare Common Procedure Coding System HCPCS code definitions.

10. The method of claim 1, further comprising providing a live chat function for use during said interaction with the one consumer for aiding in said searching and providing steps.

11. The method of claim 1, wherein said quality assessment includes a producer quality score for numerically ranking the quality of the producers.

12. A method for using a system comprising computer equipment for matching healthcare consumers to healthcare producers comprising the steps of:
 providing a producer interface to the system for each of a plurality of healthcare producers to interact with the system over the Internet;
 providing a consumer interface to the system for allowing a consumer to interact with the system over the internet;
 maintaining, on the system, a quality assessment of a plurality of said plurality of producers;
 accepting, via the producer interface, one or more available products and/or available services listings for each of the plurality of healthcare producers;
 accepting, via the consumer interface, a request from the consumer regarding a desired healthcare product or service;
 searching, using the system, the plurality of products and/or services listed by the plurality of producers for a subset of the products and/or services that are a close match to the requested desired healthcare product or service;
 providing a list of one or more items of said subset of products and/or services for display to the consumer;
 providing, when available, the quality assessment associated with each producer corresponding to each one of said one or more items for display to the consumer;
 offering said items on said list of items for purchase by the consumer; and
 for each item purchased by the consumer, performing the steps of:
  accepting payment, using the system, from the consumer for the purchased item(s),
  after the product(s) or service(s) have been provided by the producer(s) corresponding to the item(s) purchased, providing, using the system, a portion of said payment to the corresponding producer(s),
  requesting, using the system, quality information from the consumer about each of the purchased items,
  determining, using said quality information, a quality assessment of the producers that provided the purchased items based on said quality information;
  updating, using the system and using the quality information, a quality parameter for each of the producers for which the consumer provided corresponding product or service quality information such that said quality assessment allows the healthcare consumers to compare the quality of the producers against each other, and
  providing, using the system, a remaining portion of said payment, if any, to a representative of the system.

13. The method of claim 12, further comprising the step of offering a transaction guarantee to the consumer for purchase, wherein, if the consumer purchases said transaction guarantee and said quality assessment shows that one or more of the one or more product(s) and/or service(s) purchased by the one consumer did not meet a quality threshold, the system provides at least a partial refund to the consumer.

14. The method of claim 13, wherein said at least partial refund is at least partially deducted from the portion of said payment provided to the corresponding producer(s).

15. The method of claim 12, wherein said step of offering said items on said list of items for purchase by the consumer is accomplished via an auction process provided by the system to a plurality of consumers, and wherein the consumer is only offered the items for purchase if the one consumer wins the auction.

16. The method of claim 12, wherein said quality assessment includes a producer quality score for numerically ranking the quality of the producers.

17. A system for matching healthcare consumers to healthcare producers, said system comprising:
 computer hardware resources;
 a web server using at least a portion of said computer hardware resources;
 a database using at least a portion of said computer hardware resources;
 a producer subsystem using at least a portion of said computer hardware resources and utilizing said web server and database for providing a producer interface for each of a plurality of healthcare producers using producer computers to interact with the system over the Internet, wherein said producer subsystem accepts from the producer computer(s), utilizing the web server and database, one or more available products and/or available services listings from each of the plurality of healthcare producers for storing in the database;
 a consumer subsystem using at least a portion of said computer hardware resources and utilizing said web server and database for providing a consumer interface to the system for each of a plurality of healthcare consumers using computers to interact with the system over the internet, wherein said consumer subsystem accepts from at least one consumer computer, utilizing the web server and database, a request from one consumer regarding desired healthcare product or service, wherein
 at least a portion of said computer resources and information stored in the database are used for searching the plurality of products and/or services listed by the plurality of producers for a subset of said product(s) and/or service(s) that are a close match to the requested desired healthcare product or service, and wherein
 said consumer subsystem is adapted for utilizing said web server and database for providing a list of one or more items of said subset of products and/or services along with standardized quality assessments of each of the producers providing the items on the list of items for display to the one consumer on the one user computer for offering said items on said list of items for purchase by the one consumer; and further wherein
 when said system receives an indication from the user computer that one or more of the offered items is accepted for purchase by the one consumer, said system is further adapted for using at least a portion of said computer hardware resources executing software for performing the steps of:
  accepting payment information from the one consumer computer for the one or more purchased items,
  calculating a portion of said payment for providing to the producer(s) corresponding to the purchased product(s) and/or service(s),
  requesting and receiving, from the one consumer using the consumer interface, quality information about each one of the purchased one or more items, calculating a remaining portion of said payment, if any, for providing to a representative of the system, and using said information provided by the one consumer for calculating an updated standardized quality assessment for the producer(s) of the one or more purchased items.

18. The system of claim 17, further comprising an administrative subsystem using at least a portion of said computer hardware resources and utilizing said web server and database for remotely connecting to system administrators using computers over the Internet.

19. The system of claim 17, wherein payments are accepted from the one consumer, and provided to the corresponding producer(s), using a third-party payment processor.

20. The system of claim 17, wherein said standardized quality assessment associated with the corresponding producers based on quality information previously provided by other consumers is provided to the one consumer, via the one consumer computer, along with the list of one or more items.

21. The system of claim 20, wherein said consumer subsystem provides a transaction guarantee offer to the one consumer computer for purchase by the one consumer, wherein, if the system receives an indication that the consumer is purchased said transaction guarantee and said standardized quality assessment shows that one or more of the one or more product(s) and/or service(s) purchased by the one consumer did not meet a quality threshold, the system calculates at least a partial refund to be provided to the consumer.

22. The system of claim 17, wherein said offering said items on said list of items for purchase by the one consumer is accomplished via an auction process provided by the system to the plurality of consumers, and wherein the one consumer is only offered the items for purchase if the one consumer wins the auction.

23. The system of claim 17, wherein said quality assessment includes a producer quality score for numerically ranking the quality of the producers.

* * * * *

UNITED STATES PATENT AND TRADEMARK OFFICE
CERTIFICATE OF CORRECTION

PATENT NO. : 8,428,964 B2
APPLICATION NO. : 12/777302
DATED : April 23, 2013
INVENTOR(S) : Andrew J. Picken It is certified that error appears in the above-identified patent and that said Letters Patent is hereby corrected as shown below:

Title Page, item (73) Assignee: "Healthocity, Inc. A Delaware Corporation" should read
-- Healthocity, Inc. A Delaware Corporation, DBA Healthocity, Inc. --

In the Specifications
Column 43, Line 22, "Vim" should read -- Jim --
Column 43, Line 23, "Vim" should read -- Jim --
Column 43, Line 27, "Vim" should read -- Jim --
Column 43, Line 32, "Vim" should read -- Jim--
Column 43, Line 34, "Vim" should read -- Jim --
Column 43, Line 42, "Vim" should read -- Jim --

Column 44, Line 17, "Vim" should read -- Jim --
Column 44, Line 21, "Vim" should read -- Jim --
Column 44, Line 22, "Vim" should read -- Jim --
Column 44, Line 42, "Vim" should read -- Jim --
Column 44, Line 44, "Vim" should read -- Jim --

Column 45, Line 37, "Vim" should read -- Jim --
Column 45, Line 38, "Vim" should read -- Jim --
Column 45, Line 47, "Vim" should read -- Jim --
Column 45, Line 49, "Vim" should read -- Jim --

Signed and Sealed this
Fourth Day of February, 2014

Michelle K. Lee
*Deputy Director of the United States Patent and Trademark Office*